(12) United States Patent
Tanaka et al.

(10) Patent No.: US 6,423,504 B1
(45) Date of Patent: Jul. 23, 2002

(54) HUMAN-DERIVED BRADEION PROTEINS, DNA CODING FOR THE PROTEINS, AND USES THEREOF

(75) Inventors: Manami Tanaka, Ibaraki; Tomoo Tanaka, Kanagawa, both of (JP)

(73) Assignee: Secretary of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/440,936

(22) Filed: Nov. 16, 1999

(30) Foreign Application Priority Data

Nov. 16, 1998 (JP) .......................... 10-325380

(51) Int. Cl.[7] .................. G01N 33/574; C12Q 1/68; C12P 21/06; C12N 15/00; C07K 16/00
(52) U.S. Cl. .................. 435/7.23; 435/6; 435/69.1; 435/320.1; 530/388.1; 530/389.1; 530/350; 536/23.5; 424/138.1
(58) Field of Search .................. 424/138.1; 530/350, 530/388.1, 389.1; 536/23.5; 435/69.1, 7.23, 320.1, 6

(56) References Cited

U.S. PATENT DOCUMENTS 5,871,973 A * 2/1999 Hillman ............... 435/69.1
5,928,899 A * 7/1999 Hillman ............... 435/69.1

OTHER PUBLICATIONS

Albert et al., Molecular Biology of the Cell, 1989. p. 1216.*
T. Mori et al., "Isolation and mapping of a human gene (DIFF6) homologous to yeast CDC3, CDC10, CDC11, and CDC12, and mouse Diff6.", Cytogenetics and Cell Genetics, vol. 73, pp. 224–227, 1996.

Takahiro Nagase et al., "Prediction of the Coding Sequences of Unidentified Human Genes. IV. The Coding Sequences of 40 New genes (KIAA0121–KIAA0160) Deduced by Analysis of cDNA Clones from Human Cell Line KG–1.", DNA Research, col. 2, pp. 167–174, 1995.
Shuichi Nakatsuru et al., "Molecular cloning of a novel human cDNA homologous to CDC10 in *Saccharomyces cerevisiae*.", Biochemical and Biophysical Research Communications, vol. 22, No. 1, pp. 82–87, 1994.
Carol Nottenburg et al., "Lymphocyte HEV adhesion variants differ in the expression of multiple gene sequences. (Recombinant DNA;cDNA libraries; differential expression; cell surface glycoproteins)", Gene, vol. 95, pp. 279–284, 1990.

\* cited by examiner

*Primary Examiner*—Yvonne Eyler
*Assistant Examiner*—Janet L. Andres
(74) *Attorney, Agent, or Firm*—Foley & Lardner

(57) ABSTRACT

A human-derived bradeion protein, which has the following properties: (i) it is a transmembranous protein; (ii) it has a structure characteristic of growth hormone and cytokine receptors even in a structure of its transmembranous portion when its structure is determined by a hydrophobicity analysis according to Kyte-Doolittle method; (iii) it is expressed at a high level in a human adult brain, and in less amount in the heart, while it is not expressed in other adult organs or fetus; (iv) it induces programmed cell death (apoptosis) when over-expressed in a cultured human nerve cell lines; (v) it induces termination of cell division and aging when over-expressed in a cultured human normal cell; (vi) it is located in cytoplasm, and forms an intracellular aggregate when overexpressed; and (vii) besides human adult neurons, it is specifically expressed in a human colorectal cancer cell line or in a skin cancer cell line, or an analogue thereof.

18 Claims, 7 Drawing Sheets

(6 of 7 Drawing Sheet(s) Filed in Color)

Case: T8

Antisense  Sense

Case: T13

Antisense  Sense

HUMAN-DERIVED BRADEION PROTEINS, DNA CODING FOR THE PROTEINS, AND USES THEREOF

FIELD OF THE INVENTION

The present invention relates to a protein involved in long-term survival of cranial nerve cell, to DNA encoding the protein, and to uses thereof. More particularly, the present invention relates to human-derived bradeion protein or derivatives thereof, to DNA encoding the protein or the derivatives thereof, to a vector containing the DNA, to a host cell transformed or transfected with the vector, to an antibody immunologically reactive with the protein or the derivatives thereof, and to uses of the DNA or the antibody for detecting a cancer.

BACKGROUND OF THE INVENTION

Cranial nerve cells (neurons) are main elements for controlling survival of higher order animals. Once the neurons are produced, they do not divide at all and only gradually exfoliate or go through necrosis. Exfoliation of the neurons occurs in the normal state but is particularly accelerated by genetic diseases, brain ischemia, or status epilepticus, or under conditions of poor nutrition and low oxygen. Some disorders of cranial nerves associated with aging (e.g., dementia) result from deficiency of an absolute amount of functional neurons caused by accumulation of exfoliated neurons. Thus, the monitoring and control of the exfoliation, as well as regeneration of the functions of neurons, are the most demanding subject to be solved among the aging problems.

Cranial nerve cells do not divide at all after the induction phase of differentiation in the process of development, and maintain their functions or is accompanied by gradual deterioration of their functions until the end of the life-time of the individual. They are presumed to have specific division-interrupting and function-maintaining mechanisms although these mechanisms have not yet been clarified. In the central nervous system, there exist numbers of unknown proteins and signaling substances, particularly stimulating substances and receptors thereof involved in brain-specific signal transduction, but their details are yet unclear.

Numbers of researches have been conducted worldwide on such an important element that controls the survival of the cranial nerve cells. However, none of the elements was clarified in the substance or molecule level, and, prior to everything, it was necessary to develop techniques for analysis. Recently, the group of Dr. Masashi Yanagisawa and his colleagues of the University of Texas, Medical Research Center (authorized by the Howard Hughes Foundation) has succeeded in developing a technique for randomly screening neuropeptides and receptors thereof by using cultured cells, and they have found a substance (named orexin) that directly binds to and stimulates the aperitive center in the hypothalamus, and identified functions of the substance's receptor (Cell, 92, 573–585, 1998). However, such a systematic screening of substances is rare, and currently, stimulating factors involved in brain-specific signal transduction and receptors thereof are not yet fully clarified.

Under such circumstances, the present inventors have now constructed an improved expression gene (cDNA) library, developed a systematic screening technique, and succeeded in extraction and selection of genes specific for cranial nerve cells, thereby accomplishing the present invention.

Thus, one object of the present invention is to provide a bradeion protein involved in long-term survival of cranial nerve cells, and DNA coding for the bradeion protein.

Another object of the present invention is to provide a vector containing the above-mentioned DNA, and a host cell transformed or transfected with the vector.

Still another object of the present invention is to use the DNA or an antibody to the protein for detecting cancers.

SUMMARY OF THE INVENTION

The present invention provides a human-derived bradeion protein, which has the following properties:

(i) it is a transmembranous protein;

(ii) it has a structure characteristic of growth hormone and cytokine receptors (even in a structure of its transmembranous portion) when its structure is determined by a hydrophobicity analysis according to Kyte-Doolittle method;

(iii) it is expressed at a high level in the human adult brain, in less amount in the heart, while it is not expressed in other adult organs or fetus;

(iv) it induces programmed cell death (apoptosis) when over-expressed in cultured human cell lines;

(v) it induces termination of cell division and aging when over-expressed in cultured human normal cells;

(vi) it is located in cytoplasm, and forms an intracellular aggregate when overexpressed; and (vii) besides human adult neurons, it is specifically expressed in a human colorectal cancer cell line or in a skin cancer cell line, or an analogue thereof.

The proteins of the invention include Bradeion α and Bradeion β proteins having the amino acid sequences shown in SEQ ID NOS:2 and 4, respectively. These proteins are not the consequence of alternative splicing, but coded in the adjacent area (chromosome 17q23) of human genome. In addition to the above-described properties, Bradeion α induces programmed cell death when DNA coding for Bradeion α or an analogue thereof is introduced into a cultured cancer cell.

The term "analogue" as used herein refers to a protein that has properties substantially equivalent to those of the human-derived bradeion proteins (for example, at least the properties of (i), (ii), (iii), (vi) and (vii)), or a protein having an amino acid sequence with deletions, substitutions or additions of at least one amino acid residue in the amino acid sequence shown in SEQ ID NO:2 or 4, or a protein having an amino acid sequence that is substantially the same as that shown in SEQ ID NO:2 or 4. Preferably, the analogue of the invention has at least 90%, preferably at least 95%, more preferably at least 97% homology with the amino acid sequence of SEQ ID NO:2 or 4. The analogue of the invention also includes human bradeion proteins modified or mutated in the amino acid level, and bradeion proteins from non-human mammals having properties substantially equivalent to those from humans. Only Bradeion β (similar to the human-derived Bradeion β) was found, for example, in a mouse brain and its homology with the human Bradeion β was 94%. The analogues of the invention may be obtained through DNA recombinant techniques by artificial modifications (e.g., site-directed mutagenesis), as long as the original bioactivity of the human bradeion is not impaired. The analogues of the invention may or may not contain a sugar chain, or they may be chemically modified with an aqueous polymer such as polyethylene glycol.

Moreover, the present invention provides DNAs comprising nucleotide sequences coding for the above-defined bradeion proteins or analogues thereof, and fragments of the DNAs.

Specific examples of such DNAs or fragments thereof include: DNA comprising the sequence of the nucleotides 129–1943 of SEQ ID NO:1 (i.e., DNA encoding human Bradeion α); DNA fragments having at least 15, preferably at least 20, more preferably at least 30 consecutive nucleotides derived from the nucleotides 129–1943 of SEQ ID NO:1; DNA comprising the full-length nucleotide sequence shown in SEQ ID NO:1; DNA comprising the sequence of the nucleotides 129–1562 of SEQ ID NO:3 (i.e., DNA encoding human Bradeion β); DNA fragments having at least 15, preferably at least 20, more preferably at least 30 consecutive nucleotides derived from the nucleotides 129–1562 of SEQ ID NO:3; and DNA comprising the full-length nucleotide sequence shown in SEQ ID NO:3. In addition, DNA that can hybridize with one of the above-mentioned DNAs under stringent conditions is also encompassed in the present invention. The stringent conditions as mentioned herein refer to such conditions that allow hybridization only when there is at least 90% homology, preferably at least 95% homology, more preferably at least 97% homology with the nucleotide sequence shown in SEQ ID NO:1 (positions 129–1943) or SEQ ID NO:3 (positions 129–1562). Generally, such conditions allow hybridization at a temperature that is lower by about 5° C.–30° C., preferably by about 10° C.–25° C. than the melting temperature (Tm) of the complete hybrid. Stringent conditions that may be used are described in J. Sambrook et al., Molecular Cloning, A Laboratory Manual, Second Edition, Cold Spring Harbor Laboratory Press (1989), esp. "Conditions for Hybridization of Oligonucleotide Probes". The DNA and fragments thereof according to the present invention can be used not only for the expression of the bradeion proteins but also as a probe for hybridization or as a primer for PCR.

The present invention further provides vectors containing DNAs coding for bradeion proteins or analogues thereof, or fragments of the DNAS. The vector usually contains a promoter that is capable of operably expressing the DNAs. In addition to the promoter, the vector may contain at least one other element such as an origin of replication, an enhancer, a ribosome-binding site, a transcription termination factor (terminator), a selective marker, an RNA splicing site, or a polyadenylation signal.

The present invention further provides a host cell that has been transformed or transfected with such a vector. The host cell may be a prokaryotic or eukaryotic cell, preferably an eukaryotic cell, more preferably a mammalian cell such as a human cell line.

The present invention also provides an antibody that is immunologically reactive with the above-defined bradeions or analogues thereof. The antibody is preferably one that can specifically immuno-react with the bradeion proteins or analogues thereof, and is a polyclonal or monoclonal antibody.

The invention further provides a method for detecting a cancer, comprising detecting the cancer by using the above-defined DNAs or fragments thereof or the above-defined antibodies as tumor markers. Herein, the cancer includes, but is not limited to, a human colorectal cancer and a human skin cancer. The detection can be conducted by hybridization or immunoassay.

This specification includes all or part of the contents as disclosed in the specification and/or drawings of Japanese Patent Application No. 10-325380, which is a priority document of the present application.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 2A shows photographs for NT2 neuron; FIG. 2B shows photographs for NT2 neuron and HeLa; and FIG. 2C shows electron microscopic images of the cells shown in FIG. 2B (18 and 24 hours after the introduction). FIG. 2A shows locations of bradeion genes identified with EGFP (Enhanced Green Fluorescent Protein; CLONTECH Lab., Inc.) (left), locations of bradeion genes in mitochondria (center), and overlaid images of the left and center images (right).

Figure 1:
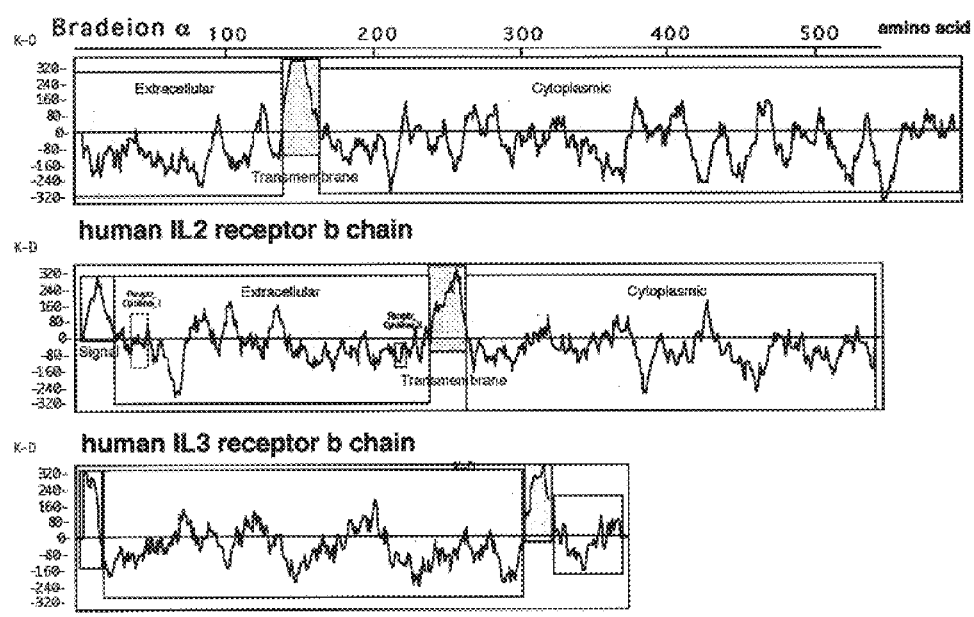
FIGS. 1A and 1B are photographs showing the results of a hydropathy analysis by the Kyte-Doolittle method, giving distributions of hydrophobic and hydrophilic portions in Bradeion α together with distributions in IL2, IL3, IL4 and growth hormone receptors for comparison.
Figure 1:
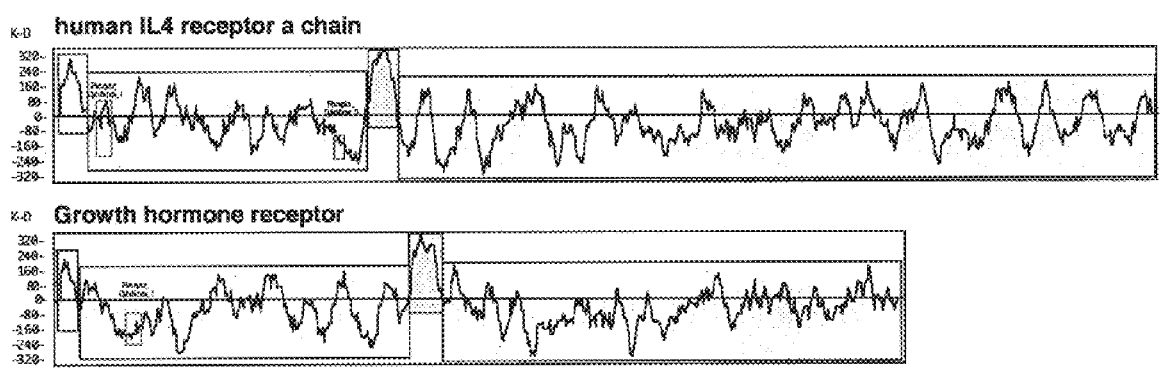

DETAILED DESCRIPTION OF THE INVENTION cDNA coding for bradeion proteins of the invention may be obtained as follows.

First, brain tissue is homogenized in a phenol or phenol-chloroform solution containing guanidine isothiocyanate, and subjected to high-speed centrifugation to be separated into an aqueous layer and an organic layer. Total RNA contained in the aqueous layer is precipitated and collected by adding isopropanol, or is collected through sucrose or cesium chloride density-gradient centrifugation. The obtained total RNA is subjected to oligo(dT)-cellulose chromatography to purify mRNA (i.e., poly(A) RNA) therefrom.

Then, cDNA is synthesized from the mRNA in the presence of a reverse transcriptase. The cDNA is provided with suitable restriction sites and inserted into a phage or plasmid vector having the identical restriction sites. The thus-obtained vector is used to transform or transfect E.coli to produce a CDNA library.

Since the cloned cDNA library includes various DNA fragments with information other than that of the DNA of interest, it is necessary to select the DNA of interest. For this purpose, plaque hybridization or colony hybridization may usually be employed. According to such methods, plaques (in the case of a phage vector) or colonies (in the case of a plasmid vector) formed on agar are transferred to a nitrocellulose membrane or a nylon membrane. After being treated with an alkaline solution, they are bound to a radioactive ($^{32}P$) or fluorescence labeling DNA probe that is capable of hybridizing with the DNA of interest, and exposed onto an X-ray film, thereby detecting and collecting a plaque or colony containing the DNA of interest. Alternatively, the obtained set of clones may be exposed to an inducer such as isopropyl 1-thio-β-D-galactoside (hereinafter, referred to as "IPTG") to forcibly express proteins. The proteins are then transferred to a nylon membrane or a cellulose membrane, and a specific antibody for the protein of interest is used to immunologically select the corresponding clones.

The cDNA of interest collected from the plaques or colonies that positively reacts with the probe is sequenced by Maxiam-Gilbert method or Sanger-Coulson method.

For cloning and sequencing, for example, methods described in Sambrook et al., Molecular Cloning (supra), Ausubel et al., Current Protocols in Molecular Biology, Green Publishing Company Assoc. and John Wiley Interscience, NY, 1992, etc. may be used.

Specifically, as will be described later in Examples, cDNA library from human adult brain is constructed and thereafter cDNA coding for the bradeion proteins of the invention are collected from the positive clones. As the result of the sequencing analysis, two types of bradeion genes, i.e., Bradeion α and Bradeion β genes, were found which were presumably produced due to alternative splicing. The nucleotide sequences of these genes are shown in SEQ ID NOS: 1 and 3, respectively, where the coding regions were at the positions 129–1943 and 129–1562, respectively. The Bradeion α and Bradeion β proteins have amino acid sequences shown in SEQ ID NOS:2 and 4, respectively, as identified from their nucleotide sequences. The Bradeion α DNA has 1815 nucleotides and codes for a protein having 605 amino acids. The Bradeion β DNA has 1434 nucleotides and codes for a protein having 478 amino acids. Met at each position 1 of the amino acid sequences of SEQ ID NOS:2 and 4 may be present or absent. When these nucleotide and amino acid sequences were compared to all sequences deposited with the GenBank, it was found that the Bradeion α and Bradeion β genes and proteins were novel.

Bradeion α and Bradeion β proteins were found to have a structure characteristic of an interleukin receptor even in a structure of its transmembranous portion, when subjected to the hydropathy analysis according to Kyte-Doolittle method (J. Mol. Biol., 157 (1): 105–132, 1982). Thus, it has the structure of a transmembrane-type receptor that is presumably involved in the intracellular signaling mechanism. Bradeion α and Bradeion β proteins are also similar to the relationship of the tumor suppression genes p53/p73 in that there are two types of expression modes, i.e., α- and β-types, and in that either of them is prevalent in various organisms.

Formation of an intracellular aggregate is very similar to that seen in human nerve retroplasia caused by a triplet repeat gene expressed substance (Igarashi et al., Nature Genetics, 111–117, 1998; Martindale et al., Nature Genetics, 150–154, 1998). Accordingly, it is assumed that the Bradeion α and Bradeion β proteins are greatly associated with specific termination of the division of human nerve cells and/or with maintenance of the function of the nerve cells after development/differentiation in the normal gene expression state.

The human-derived bradeion proteins or analogues thereof of the invention may be obtained, for example, by using gene recombinant techniques as follows.

Taking account of degeneracy of the genetic codes, a hybridization probe having at least 15, preferably about 20 to about 50 consecutive nucleotides is constructed based on the nucleotide sequence shown in SEQ ID NO:1 or 3 or the amino acid sequence shown in SEQ ID NO:2 or 4. By using this hybridization probe, DNAs coding for the bradeion proteins are screened from a genomic DNA library or cDNA library derived from human or non-human mammal brain tissue. The library may be produced by using commercially available vector such as λ ZAPII or pBluescript® cloning vector (Stratagene Cloning Systems). The plaque or colony containing the DNA of interest is selected through plaque hybridization or colony hybridization.

Alternatively, a DNA sequence generally having 15 to 100 consecutive nucleotides complementary to the nucleotides 129–1943 of SEQ ID NO:1 or the nucleotides 129–1562 of SEQ ID NO:3, is produced as a primer. This primer can be used to conduct polymerase chain reaction (PCR) in the genomic DNA library or cDNA library derived from human or non-human mammalian brain tissue, thereby specifically amplifying the DNA of interest. PCR can be conducted through at least 20 cycles, preferably at least 30 cycles of: denaturation at 94° C. for 1 min.; annealing at 57° C. for 2 min.; and elongation at 70° C. for 3 min. For the PCR, see the techniques described in Protein Nucleic acid and Enzyme, "Frontier of PCR method—Basic to Applied Techniques" vol. 4(5), April, 1996 Supplement, Kyoritsu Shuppan, Tokyo, Japan.

The cloned or amplified DNA of interest is collected and introduced into an available suitable expression vector. The obtained vector is used to transform a suitable host cell, which is thereafter cultured in a proper medium for expression of the DNA, to isolate and purify the protein of interest.

Examples of the analogue of the present invention include: a protein having a substantially equivalent properties to the human-derived bradeion (especially, at least the above-mentioned properties of (i), (ii), (iii), (vi) and (vii)); or a protein having an amino acid sequence with deletions, substitutions or additions of at least one amino acid residue in the amino acid sequence shown in SEQ ID NO:2 or 4; or a protein having an amino acid sequence that is substantially the same as that shown in SEQ ID NO:2 or 4. Preferably, the analogue has at least 90%, preferably at least 95%, more preferably at least 97% homology with the amino acid sequence shown in SEQ ID NO:2 or 4. This means that the amino acid sequence of the analogue may include a modification chosen from deletion, substitution or addition of at least one amino acid as long as the analogue has properties substantially equivalent to those of the human Bradeion α or Bradeion β. The mutation may be introduced into the amino acid sequence shown in SEQ ID NO:2 or 4 through genetic engineering, for example, by well-known techniques such as site-directed mutagenesis/PCR method (S. N. Ho et al., Gene, 77, 51, 1989); and methods described in Kaoru Saigo and Yumiko Sano (trans.), Current Protocols compact version, Experimental Protocols in Molecular Biology I, June 1997, Maruzen, Tokyo, Japan). Examples of the substitution include substitutions between hydrophobic amino acids (Ala, Val, Leu, Ile, etc.), Ser and Thr, Asp and Glu, Asn and Gln, Lys and Arg, and Phe and Tyr. Examples of the addition include an addition of Met to the N-terminus of a mature protein as seen in products expressed in a bacterial host, and an addition of His-tag, or Met-Lys or Met-Arg sequence to the N-terminus for facilitating induction of a mature protein. It is also possible to truncate some amino acid residues at the carboxyl or amino terminus of the bradeion protein to an extent where bioactivity is not impaired.

Proteins without sugar chains are produced when a prokaryotic cell such as bacterium is used as the host cell for expressing DNAs coding for the bradeion proteins or analogues thereof through genetic engineering. On the other hand, products with sugar chains may be produced when the DNAs are expressed in an eurokaryotic cell such as fungus, yeast, insect, plant, or mammalian cell. For example, sugar chains may be formed by introducing an N-binding sugar chain site (generally, Asn-Xaa-Thr/Ser where Xaa is any amino acid other than Pro) into the sequence. In any event, the obtained analogue should have bioactivity substantially equivalent to the human bradeions.

Amino groups at the N-terminus or $\epsilon$-amino groups of lysine of the human bradeion proteins or analogues thereof of the invention may be chemically bound to an aqueous polymer such as polyethylene glycol (PEG). Pegylation is generally known to reduce or suppress antigenicity or immunogenisity upon in vivo administration of a pegylated product.

The present invention further provides an expression vector containing the above-described DNA, and a host cell transformed or transfected with the vector.

The vector of the invention may be in the form of, for example, plasmid, phage, or virus. Other types of vectors may also be used as long as they are replicable in a host cell. For example, bacterium plasmids (e.g., pBR322, pKC30, pCFM536, etc.), phage DNAs (e.g., λ phage, etc.), yeast plasmids (e.g., pG-1, etc.), or viral DNAs for mammal host cells (e.g., baculovirus, vaccinia virus, adenovirus, SV40 and its derivatives, etc.) may be used.

The vector usually contains a replication origin, a selective marker, a promoter, and, if necessary, may contain an enhancer, a transcription termination sequence (terminator), a ribosome-binding site, a polyadenylation signal, etc.

Where the vector is used for *E.coli*, the replication origin is derived from ColE1, R factor, or F factor. Where the vector is used for yeast, the replication origin is derived from, for example, 2 μm DNA or ARS1. Where the vector is used for a mammalian cell, the replication origin is derived from, for example, SV40, adenovirus, or bovine papilloma virus.

The promoter is a regulator sequence for directing a synthesis of mRNA coding for the DNA of the invention. Representative examples of the promoter include adenovirus or SV40 promoter, *E.coli* lac or trp promoter, phage $\lambda P_L$ promoter, ADH, PHO5, GPD, PGK or AOX1 promoter (for yeast), and a promoter derived from nuclear polyhedrosis virus (for *Bombyx mori* cell).

The selective marker is a gene for providing a phenotype to the host in order to select transformed host cells. Exemplary selective markers include kanamycin-resistant gene, ampicillin-resistant gene, tetracycline-resistant gene, and the like (when the vector is used for *E.coli*); Leu2, Trp1, Ura3 genes, and the like (when the vector is used for yeasts); and neomycin-resistant gene, thymidine kynase gene, dihydrofolate reductase gene, and the like (when the vector is used for mammalian cells).

Commercially available vectors may be used such as pQE70, pQE60, pQE-9 (Qiagen), pBluescript II KS, ptrc99a, pKK223-3, pDR540, pRIT2T (Pharmacia), and pET-11a (Novagen) as bacterium vectors; and pXT1, pSG5 (Stratagene), pSVK3, pBPV, pMSG and pSVL SV40 (Pharmacia) as eukaryote vectors.

The DNA of the invention may be introduced into the vector by any means. The vector preferably contains a polylinker with various restriction sites, or a unique restriction site. The DNA of the invention is inserted into a particular restriction site(s) of the vector where it has been cleaved with a particular restriction endonuclease(s).

The expression vector containing the DNA of the invention with a regulatory sequence is used to transform or transfect a suitable host cell, thereby expressing and producing the human bradeion protein of the invention or an analogue thereof in the host cell.

The host cell is, for example, a bacterial cell (e.g., *E.coli*, streptomyces, or *Bacillus subtilis*), an eukaryotic cell (e.g., Aspergillus strain), an yeast cell (e.g., *Saccharomyces cerevisiae*, or methanol-assimilating yeast), an insect cell (e.g., Drosophila S2 or Spodoptera Sf9), and a mammalian cell including cultured human cell (e.g., CHO, COS, BHK, 3T3, or C127).

Transformation or tranfection may be conducted by a known method such as calcium chloride/rubidium chloride method, calcium phosphate method, DEAE-dextran-mediated transfection, or electroporation.

The human-derived bradeion or an analogue thereof of the invention can be obtained by culturing the host cells which have been transformed or transfected as described above under the control of the promoter, and by collecting the produced protein of interest. The host cell is amplified or grown to a proper cell density. Then, the promoter is induced by shifting the temperature or by chemical induction (with IPTG, etc.). The cell is further cultured for a predetermined period. Where the protein of interest is secreted extracellularly, it can directly be obtained from the medium. Where the protein of interest is present intracellularly, the cell can be disrupted by physical means (e.g., sonication or mechanical disruption) or by chemical means (e.g., lyzozyme or cytolytic agent). Then the protein of interest is purified. The protein may partially or completely be purified from the culture medium containing the recombinant cells or an extracted solution thereof, by using routine techniques such as ammonium sulfate or ethanol precipitation, acid extraction, anion or cation exchange chromatography, hydrophobic interaction chromatography, affinity chromatography, gel filtration chromatography, HPLC, electrophoresis, and chromatofocusing, alone or in combination.

The DNA of the invention was gene-transferred into several human cell lines or cancer cell lines to examine the functions of the bradeion proteins. As a result, in addition to the above-described findings, the following facts were found out:

(1) when the DNA of the invention is gene-transferred into NT2 neuron (Stratagene), which is a cultured human undifferentiated nerve cell, using Superfect reagent (Qiagen) and over-expressed, the cell death is induced within 18–24 hours.

(2) when the DNA is similarly over-expressed in cultured human normal cells, termination of the aging and cell division is induced.

(3) when the DNA is gene-transferred into a cultured cancer cell, Bradeion α and Bradeion β genes induce the programmed cell death.

(4) in the course of the induced cell death, the bradeion protein is present in cytoplasm, and forms an intracellular aggregate.

As a result of studies using cultured human cancer cell lines, the expression of bradeion was detected to be specific for colorectal cancer and malignant melanoma (skin cancer), suggesting that it has strong preferability for tissues and cell types in which bradeion genes are expressed.

Based on the above-described findings, the bradeion proteins of the invention seem to allow survival of cranial nerve cells of the central nervous system in non-dividing state via neuro-stimulating transmission. It seems to be important that over-expression of the bradeion genes controls cell fate: apoptosis or carcinogenesis, and that normally the expression ratio of the α-type to the β-type is maintained (at a ratio of 10:1 in a normal cranial nerve cell). It was also suggested that depending on changes in the expression ratio (e.g., 1:1), it may induce development of cancer. Accordingly, the bradeion proteins are presumed to play an important role in controlling cell fate (termination, apoptosis, and/or carcinogenesis), and also to determine long-term survival of cranial nerve cells in non-dividing state in human adult central nervous system. Thus, the bradeion proteins are useful for monitoring exfoliated nerve cells associated with aging, studying necrosis of nerve cells that occurs during brain ischemia and status epilepticus, and understanding the survival mechanism of neurons and pathology of brain. The proteins are also useful for producing novel medicines for treating genetic diseases, and may be applied to genetic diagnosis and gene therapy of cancers.

Thus, the proteins of the invention or fragments thereof, antibodies to them, or the DNAs of the invention or fragments thereof may be used for detecting or diagnosing cancers (e.g., human colorectal carcinoma and human skin cancer), for determining the cell fate, and as a targeting molecule in colorectal cancer and malignant melanoma.

For the above purposes, a polyclonal or monoclonal antibody that is specific to the proteins of the invention is useful. The antibody, preferably the monoclonal antibody, may be used for diagnosis, vaccination and drug delivery systems.

Such antibodies may be produced, for example, by methods described in Suguru Matsubasi et al., Biochemical Experimental Methods 15, Introduction to Immunological Experiments, 1982, Japan Scientific Societies Press, Tokyo, Japan; Tatsuo Iwasaki et al., Monoclonal antibody-Hybridoma and ELISA, 1987, Kodansha Scientific, Tokyo, Japan.

The polyclonal antibody can be obtained as follows. First, an antigen solution containing the protein of the invention or a fragment thereof as an antigen is mixed with complete Freund's adjuvant to form an emulsion. The emulsion is then subcutaneously injected into a mammal such as rabbit, mouse, goat, bovine or equine. After about 2 weeks, an antigen solution emulsified in incomplete Freund's adjuvant is similarly injected into the animal, which is then boosted if necessary, and blood is drawn from the animal to collect anti-serum as the polyclonal antibody. The anti-serum is further subjected to ammonium sulfate precipitation or ion exchange chromatography using DEAE cellulose to obtain an IgG fraction. The IgG is subjected to an affinity chromatography on CNBr-activated Sephadex or Sepharose bound to the protein of the invention or a fragment thereof to mono-specifically purify the antibody of interest that is bound through immunologic reaction.

The monoclonal antibody can be obtained as follows. First, an antigen-adjuvant emulsion is prepared as described above, which is then intraperitoneally injected into a mouse (e.g., BALB/c) for immunization. The spleen was removed from the mouse to collect spleen cells, which are then fused with a myeloma cell (e.g., X63 or NS-1) in the presence of polyethylene glycol (e.g., PEG 400). Then, an antibody-producing hybridoma is selected in an HAT medium to obtain the monoclonal antibody of interest by a cloning method or alternatively from ascites obtained from the mouse after the intraperitoneal injection. Humanized monoclonal antibody may also be prepared by using known techniques as described in Teng et al., Proc. Natl. Acad. Sci. USA, 1983, 80:7308–7312, and Kozbor et al., Immunology Today, 1983, 4 (3): 72–79.

The above-described antibody may be used for diagnosing, for example, cancers in a standard immunoassay such as an enzymatic immunoassay, a radioimmunoassay or a fluorescent antibody method.

Where the DNA of the invention or a fragment thereof is used as a probe or a primer, at least 15, preferably at least 20, more preferably at least 30 consecutive nucleotides derived from the nucleotide sequence of SEQ ID NO:1 (the nucleotides 129–1943) or SEQ ID NO:3 (the nucleotides 129–1562) can be prepared using an automatic DNA synthesizer. The obtained nucleotide fragment is labeled with an isotope, a fluorescent substance or the like, thereby preparing a probe or a PCR primer for diagnosis. The conditions employed for hybridization are, for example, described in Sambrook et al., Molecular Cloning (supra), and F. M. Ausubel et al., Short Protocols In Molecular Biology, Third Edition, John Wiley & Sons.

EXAMPLES

Hereinafter, the present invention will be described by way of examples. The present invention, however, is not intended to be limited to these examples.

Example 1

Cloning and Sequencing of cDNA Coding for Human Bradeion

First, a cDNA library from a human adult brain was constructed using the plasmid vector pCMV SPORT1 (Life Technologies, Inc., USA) which is capable of linking with a CMV promoter for expressing in an eukaryotic cell. The adult brain was obtained from a 36-year-old white Caucasian American female, and mRNA (poly(A) RNA) was extracted therefrom with TRIzol® reagent (Life Technologies, Inc.) and purified with MESSAGEMAKER® reagent (Life Technologies, Inc.). Then double stranded cDNA synthesis and library construction were initiated by SuperScript plasmid system.

The prepared mRNA (poly(A) RNA) was linked with NotI primer adapter at its 3'-terminus. Then, a double stranded cDNA was synthesized according to a standard method using Superscript II reverse transcriptase and T4 DNA polymerase. The 5'-terminus of the CDNA was linked with SalI adapter and 3'-terminus was treated with NotI restriction enzyme so that the CDNA fragment had restriction sites SalI and NotI at each end. The cDNA was separated in sizes by gel filtration chromatography to select and fractionate cDNA having a size of 1 kb or more. The obtained set of cDNA fragments was inserted, by a standard method, into the plasmid vector PCMV SPORT1 that also had been cleaved with SalI and NotI, thereby producing circular plasmids. These plasmids were introduced into *E.coli* DH12S cells (Life Technologies, Inc.) by an electroporation method and amplified to construct a library.

The resulting *E. coli* strains were grown on ampicillin-containing LB agar medium to form colonies. Biodyne A nylon membrane (Pall Corp., US) treated with 10 mM IPTG was placed in close contact with the colonies and left at 37° C. for 2 hours. The nylon membrane was reacted with the antibody CE5 that specifically recognizes cranial nerve cells [Nature, 296, 34–38, 1982]. Positive clones were selected using picoBlue® Immunoscreening Kit (Stratagene, US).

Plasmid DNA was collected from the obtained positive clones to be used as a $^{32}$P-labeled probe, which was hybridized with nylon membranes with mRNAs specific for different human organs (MTN blot, CLONTECH Lab., Inc.) to test whether the probe was specific for the brain. The nucleotide sequences of the cDNAs were determined by sequencing analysis and compared with homologous sequences deposited with the GenBank. Only the one that was completely novel was deposited with the GenBank as a sequence of interest. The determined nucleotide sequence of the Bradeion α cDNA is shown in SEQ ID NO:1 (GenBank Accession No. AB002110). The coding region was at the positions 129–1943. The amino acid sequence of the Bradeion α determined based on this nucleotide sequence is shown in SEQ ID NO:2. DNA containing Bradeion α cDNA was deposited with the National Institute of Bioscience and Human-Technology, Agency of Industrial Science and Technology (Higashi 1-1-3, Tsukuba-shi, Ibaraki-ken 305-8566, Japan) on Jul. 14, 1998 as FERM P-16897. (This deposit was thereafter transferred to an international deposition under the terms of Budapest Treaty on Oct. 19, 1999 and was given an Accession No. FERM BP-6922.)

Based on the above-described sequence of Bradeion α CDNA, 5'-terminal primers (described below) were synthesized to systematically screen relevant genes. For this purpose, Gene Trapper Positive Selection system (Life Technologies, Inc.) was used to screen the above-described gene library with the synthesized oligonucleotides and magnet beads. The sequences of the oligonucleotides used were:

5'-ctgagcaagttcgtgaaggatttc-3' (SEQ ID NO:5); and

5'-cagtcctctgacaaccagcagta-3' (SEQ ID NO:6)

As a result, a gene was detected which was named Bradeion β and whose nucleotide sequence is shown in SEQ ID NO:3 (GenBank Accession No. AB008753). The coding region was at the positions 129–1562. The amino acid sequence of Bradeion β determined based on this nucleotide sequence is shown in SEQ ID NO:4.

Example 2

Characterization of Bradeion α and Bradeion β Proteins (1) Hydropathy Analysis

The amino acid sequences of Bradeion α and β proteins determined in Example 1 were subjected to hydropathy analysis by Kyte-Doolittle method (Kyte, J. and Doolittle, R. F. J., J. Mol. Biol., 1982, 157 (1): 105–132). This analysis is one method for predicting a high-order structure of a protein based on its amino acid sequence, whereby the distributions of hydrophobic and hydrophilic portions of the protein can be determined. This analysis therefore allows to study the presence of a three-dimensional structure or a transmembranous domain. FIGS. 1A and 1B show the results of the analysis for the bradeion proteins as well as the results for human-derived IL (interleukin) 2, IL3 and IL4 receptors and growth hormone receptor for comparison. Referring to the figures, the proteins having the sequences of growth hormone and cytokine receptors may be divided roughly into three sections, i.e., an assembly of hydrophobic groups (calculated as positive ("+") values) as a transmembranous portion (third column from the left, shown in red), an extracellular portion (second column from the left, shown in blue) preceding the transmembranous portion, and a cytoplasmic portion (fourth column from the left, shown in green) following the transmembranous portion. This structure is common among all of the receptors including the bradeion proteins of the invention. However, bradeion proteins did not have a hydrophobic signal peptide (first column from the left, shown in yellow).

As a result, the bradeion proteins of the invention were found to be membrane proteins with a structure characteristic of an interleukin receptor even in the structure of a transmembranous portion in the amino acid sequences.

(2) Localization of Bradeion Proteins

Hybridization with the nylon membranes with mRNAs specific for different human organs (MTN blot, CLONTECH Lab., Inc.) indicated a high level expression only in the human adult brain, and a low level of expression in the heart ($\leq 10\%$ of the expression level in the brain). No expression was seen in other organs or in human fetus. Both of the α- and β-types were expressed in the adult brain. The difference in types was due to the gene duplication in the adjacent area (17q23) of human chromosome. A homologous gene sequence, but only one of the two types of human bradeions (i.e., Bradeion β) existed in the mouse brain (94% homology).

(3) Experiment of Overexpression of Bradeion α and Bradeion β Genes in Cultured Human Cell Lines Bradeion α and Bradeion β DNAs were individually gene-transferred into NT2 neuron (Stratagene, US), which is a cultured human undifferentiated nerve cell line, with Superfect reagent (QIAGEN, US) and over-expressed. The results are shown in FIGS. 2A, 2B and 2C.

Figure 2:
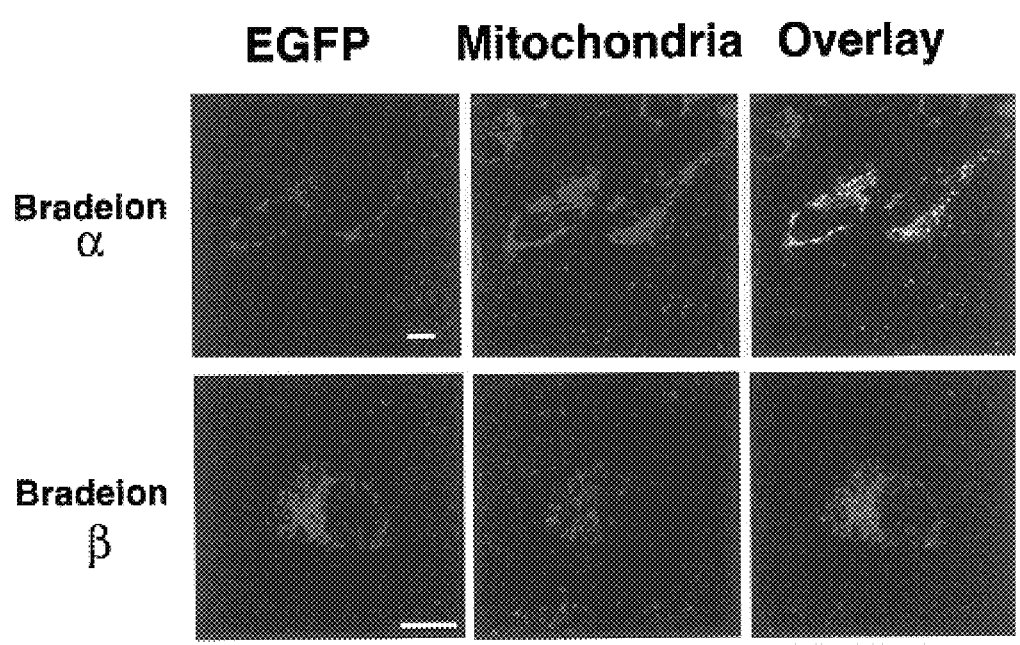
FIGS. 2A–C are photographs taken with a confocal laser microscope showing images of labeled cells observed by gene-transfer and over-expression of Bradeion α and Bradeion β genes in cultured NT2 neuron (human undifferentiated nerve cell) and HeLa cell.
Figure 2:
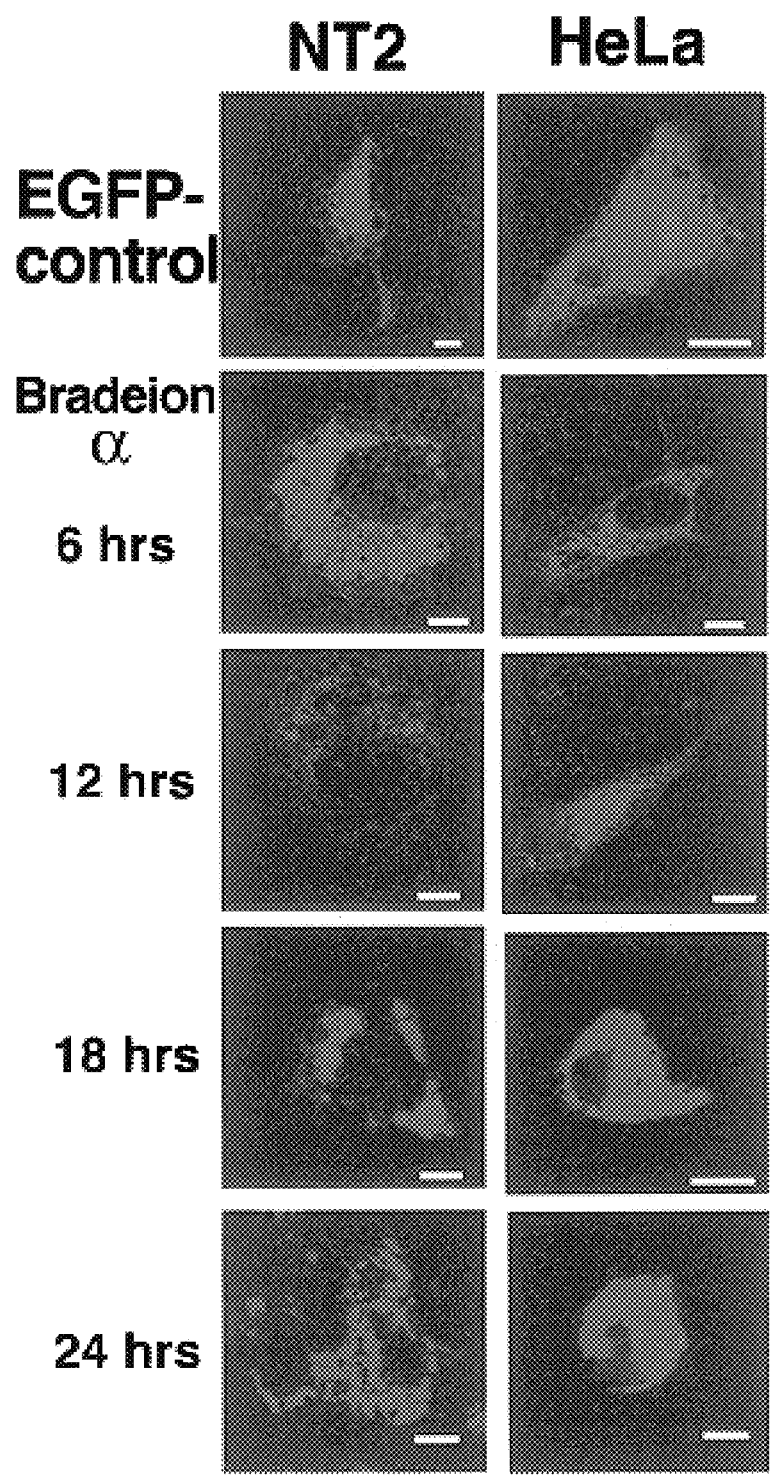
Figure 2:
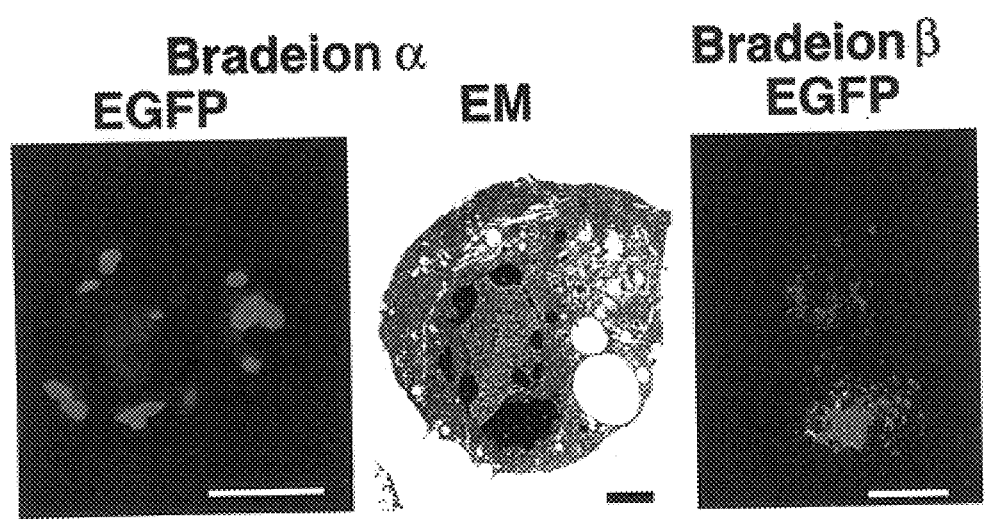

FIG. 2A shows images of the labeled cell observed 24 hours after overexpression of Bradeion α gene (upper panels) and Bradeion β gene (lower panels). The left images show the locations of Bradeion α and Bradeion β. The center images show their locations in mitochondria, and the right images show the overlaid images of the left and center images. All of the images were observed with a confocal laser microscope. As a result, it was found that the location of Bradeion α was consistent with the location in mitochondria (Note: yellow color indicates an overlap of red and green.) while the location of Bradeion β was not consistent with the location in mitochondria.

Programmed cell death (apoptosis) was induced within 18–24 hours after the transfection of the Bradeion α gene. In the course of the apoptosis, Bradeion α formed an intracellular aggregate. FIG. 2B shows cell images observed at predetermined points of time after the gene transfer. The left images show the cultured human cell NT2 neuron (Stratagene) and the right images show the human cancer cell line, HeLa. Both cell lines formed intracellular aggregates, resulting in cell death. To confirm this fact, the cells of FIG. 2B were observed with an electron microscope. As shown in FIG. 2C, the presence of apoptosis corpuscles specific for programmed cell death (apoptosis) was confirmed.

(4) Correlation of Bradeion α and Bradeion β Genes to Cancers

Although the Bradeion α and Bradeion β genes are only expressed in the normal adult brain and the heart (about 10% of the expression level of the brain), their expression was also found in cultured human cancer cell lines. The results are shown in FIGS. 3A, 3B and 3C.

Figure 3:
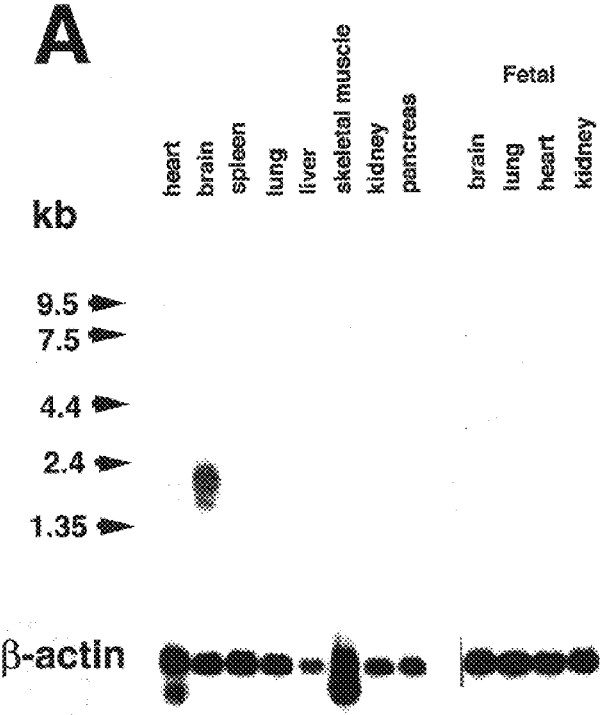
FIG. 3A is a photograph showing expression of equal amounts of Bradeion α and Bradeion β genes in human cancer cell lines, giving the results of Northern blot analysis using radiolabeled bradeion genes. Lane 1 shows expression in polymyelocytic leukemia, HL60; Lane 2 shows expression in HeLaS3; Lane 3 shows expression in chronicmyologenous leukemia, K-562; Lane 4 shows expression in lymphoblastic leukemia, MOLT-4; Lane 5 shows expression in Burkitt's lymphoma, Raji; Lane 6 shows expression in colorectal adenocarcinoma, SW480 21, 22; Lane 7 shows expression in lung carcinoma, A549; and Lane 8 shows expression in melanoma, G361. The result of Northern blot analysis using a β-actin gene is shown underneath as a positive control.
FIG. 3B shows cancer-specific expression of bradeion genes in colorectal adenocarcinoma cell (T1 to T10); skin cancer cells (T11 to T13); and normal cells (N1 to N2). All specimens are from humans. In the figure, "*" refers to the case where both Bradeion α and Bradeion β genes are detected without gene mutation; "ND" refers to the case where detection was impossible due to denaturation of RNA; "Ad (well)" refers to a well differentiated adenocarcinoma; "Ad (mod)" refers to a moderately differentiated adenocarcinoma; "Muc" refers to a mucinouscarcinoma; and "MM" refers to malignant melanoma. Dukes' stage is based on the Dukes' classification. Codon 12 of human K-ras gene (whose wild type sequence is GGT) is indicated if it has been mutated. This mutation is heterozygous.
FIG. 3C is photographs of the results of in situ hybridization of specimens from human cancer tissue, showing stained tissues for T13 and T8 (FIG. 3B) (Antisense: positive control, Sense: negative control).
Figure 3:
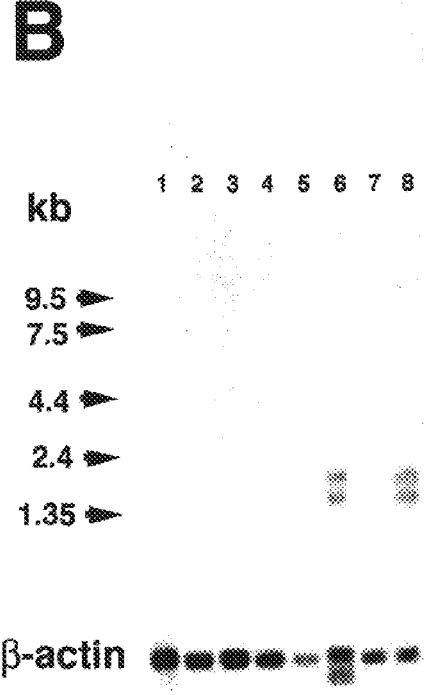
Figure 3:
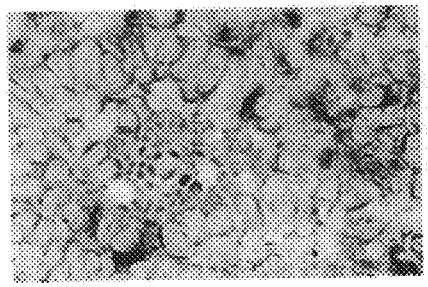
Figure 3:
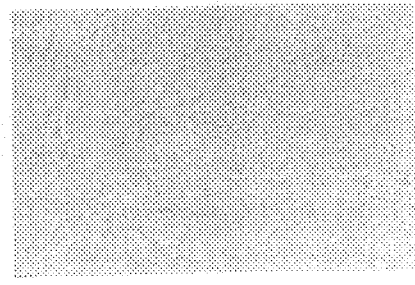
Figure 3:
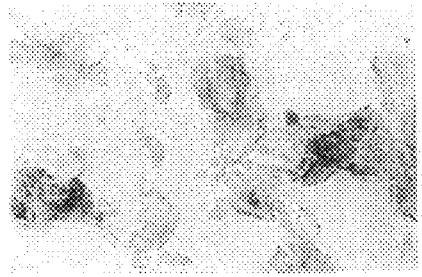
Figure 3:
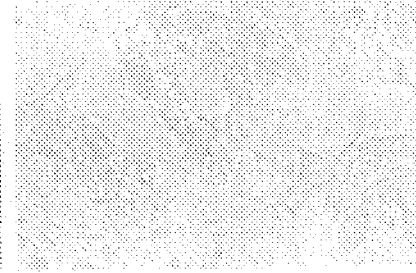

FIG. 3A shows the results of Northern blot regarding expression of Bradeion α and Bradeion β genes in different cultured human cancer cells. Specific expressions (signals) were found only in Lane 8 (skin cancer cell line G361) and Lane 6 (colorectal adenocarcinoma SW480).

Specimens from human patients (i.e., specimens from pathologic tissues) were used for detection of the cancer-specific expression. As shown in FIG. 3B, the specific expression was observed in 10 specimens having colorectal adenocarcinoma (T1 to T10; indicated as Ad), and in 3 specimens having skin cancer (T11 to T13; indicated as Muc and MM). FIG. 3C shows images of stained cancer cells for confirming the cancer-specific expression.

The above results show that the Bradeion α and Bradeion β proteins and the genes encoding them can be used as tumor-specific markers of colorectal cancer.

ADVANTAGEOUS EFFECT OF THE INVENTION

The bradeion proteins of the invention and the DNA encoding them seem to allow survival of cranial nerve cells of the central nervous system in non-dividing state via neuro-stimulating transmission. Over-expression of the bradeion genes induces apoptosis. Normally, the in vivo expression ratio of Bradeion α and Bradeion β proteins is maintained (at a ratio of 10:1 in a normal cranial nerve cell). It is also suggested that depending on changes in the expression ratio (e.g., 1:1), the development of a cancer may be induced. Accordingly, the bradeion proteins and the DNA encoding them were presumed to act as a cell-lifetime-prolonging, cancer-development-suppressing factor that determines long-term survival of cranial nerve cells in non-dividing state after the development/differentiation of the cells. Thus, they are useful for monitoring exfoliated nerve cells associated with the aging, studying the necrosis of nerve cells that occurs during brain ischemia and status epilepticus, and understanding the survival mechanism of the central nerve cells and pathology of brain. They are also useful for producing novel medicines for treating genetic diseases, and may be applied to genetic diagnosis and gene therapy of cancers.

All publications (including patent application) cited herein are incorporated herein by reference in their entirety.

The following are information on SEQ ID NOS:1 to 4 described herein:

```
SEQ ID NO:1 gaaaggagca agccaggaag ccagacaaca acagcatcaa aacaaggctg tttctgtgtg   60
tgaggaactt tgcctgggag ataaaattag acctagagct ttctgacagg gagtctgaag  120
cgtgggacat ggaccgttca ctgggatggc aagggaattc tgtccctgag gacaggactg  180
aacctgggat caaccgtttc ctggaggaca ccacggatga tggagaactg agcaagttcg  240
tgaaggattt ctcaggaaat gcgagctgcc acccaccaga ggctaagacc tgggcatcca  300
ggccccaagt cccggagcca aggcccagg ccccggacct ctatgatgat gacctggagt  360
tcagaccccc ctcgcggccc cagtcctctg acaaccagca gtacttctgt gccccagccc  420
ctctcagccc atctgccagg ccccgcagcc catgggggga gcttgatccc tatgattcct  480
ctgaggtaga gcctccagcc ctgcctttgc ctttcagtgg gctgctgcag gaagaccggg  540
ggcagggagc aggaatgtgt gtgtgtgtgt gtgtgtgtgt gtgtgtgtgt gtgtttgtgt  600
gtgtgtgtat ctgggaccca tttcagtcct gtgtcagccc tagctccaaa atatctgccc  660
ccaaggggac tggaaatttg cagtttcagc aagggcagga ggcccagctg gtggcctcag  720
atgggaactc acagaagtct ggcactgctt ttttaaggct ggggcaaagg cctgaaaggg  780
agagaagatt ggcgctgggt gccggggccc ctttggctcc tcaccgtgat gcattctgcc  840
ttcctgtcta ctacgatgac aaggagtatg tgggctttgc aaccctcccc aaccaagtcc  900
accgaaagtc cgtgaagaaa ggctttgact ttaccctcat ggtggcagga gagtctggcc  960
tgggcaaatc cacacttgtc aatagcctct tcctcactga tctgtaccgg gaccggaaac 1020
ttcttggtgc tgaagaaagg atcatgcaaa ctgtggagat cactaagcat gcagtggaca 1080
tagaaaaaaa aggtgtgagg ctgcggctca ccattgtgga cacaccaagt tttggggatg 1140
cagtcaacaa cacagagtgt atgtctgact ggaagcctgt ggcagaatac attgatcagc 1200
agtttgagca gtatttccga gacgagagtg gcctgaaccg aaagaacatc caagacaaca 1260
```

-continued

```
gggtgcactg ctgcctgtac ttcatctcac ccttcggcca tgggctccgg ccattggatg  1320
ttgaattcat gaaggccctg catcagcggg tcaacatcgt gcctatcctg ctaaggcag   1380 acacactgac acctcccgaa gtggaccaca agaaacgcaa aatccgggag gagattgagc  1440
attttggaat caagatctat caattcccag actgtgactc tgatgaggat gaggacttca  1500
aattgcagga ccaagcccta aaggaaagca tcccatttgc agtaattggc agcaacactg  1560
tagtagaggc cagagggcgg cgagttcggg gtcgactcta cccctggggc atcgtggaag  1620
tggaaaaccc agggcactgc gactttgtga agctgaggac aatgctggta cgtacccaca  1680
tgcaggacct gaaggatgtg acacgggaga cacattatga gaactaccgg gcacagtgca  1740
tccagagcat gacccgcctg gtggtgaatg aacggaatcg caagtatgac cagaagccag  1800
gacaaagctg gcaggggag atcccaagcc tagccttggg tgagaccaag ccctacttt   1860 gttcttctat aggccctggg ctcaatctaa gcgggtgctg gggtcctcct cgccttatca  1920
acccttttct cccctttagca aactgactcg ggaaagtggt accgacttcc ccatccctgc  1980
tgtcccacca gggacagatc cagaaactga gaagcttatc ccagagaaag attaggagct  2040
gcggcggata cacgagatac tacaccaaat accaaaacag ataaaggaga actatttact  2100
ggctttcagc cctggatatt taaatctcct cctcttcttc ctgtccatgc cggcccctcc  2160
cagcaccagc tctgctcagg ccccttcagc tactgccact tcgccttaca tccctgctga  2220
ctgcccagag actcagagga aataaagttt aataaatctg taggtggctt ctgg        2274
```

SEQ ID NO:2

```
Met Asp Arg Ser Leu Gly Trp Gln Gly Asn Ser Val Pro Glu Asp Arg
 1               5                  10                  15

Thr Glu Pro Gly Ile Asn Arg Phe Leu Glu Asp Thr Thr Asp Asp Gly
             20                  25                  30

Glu Leu Ser Lys Phe Val Lys Asp Phe Ser Gly Asn Ala Ser Cys His
         35                  40                  45

Pro Pro Glu Ala Lys Thr Trp Ala Ser Arg Pro Gln Val Pro Glu Pro
     50                  55                  60

Arg Pro Gln Ala Pro Asp Leu Tyr Asp Asp Leu Glu Phe Arg Pro
 65                  70                  75              80

Pro Ser Arg Pro Gln Ser Ser Asp Asn Gln Gln Tyr Phe Cys Ala Pro
             85                  90                  95

Ala Pro Leu Ser Pro Ser Ala Arg Pro Arg Ser Pro Trp Gly Glu Leu
            100                 105                 110

Asp Pro Tyr Asp Ser Ser Glu Val Glu Pro Pro Ala Leu Pro Leu Pro
        115                 120                 125

Phe Ser Gly Leu Leu Gln Glu Asp Arg Gly Gln Gly Ala Gly Met Cys
    130                 135                 140

Val Cys Val Cys Val Cys Val Cys Val Phe Val Cys Val Cys
145                 150                 155                 160

Ile Trp Asp Pro Phe Gln Ser Cys Val Ser Pro Ser Lys Ile Ser
                165                 170                 175

Ala Pro Lys Gly Thr Gly Asn Leu Gln Phe Gln Gln Gly Gln Glu Ala
            180                 185                 190

Gln Leu Val Ala Ser Asp Gly Asn Ser Gln Lys Ser Gly Thr Ala Phe
        195                 200                 205

Leu Arg Leu Gly Gln Arg Pro Glu Arg Glu Arg Leu Ala Leu Gly
    210                 215                 220

Ala Gly Ala Pro Leu Ala Pro His Arg Asp Ala Phe Cys Leu Pro Val
```

-continued

```
                225                 230                 235                 240
Tyr Tyr Asp Asp Lys Glu Tyr Val Gly Phe Ala Thr Leu Pro Asn Gln
                    245                 250                 255
Val His Arg Lys Ser Val Lys Lys Gly Phe Asp Phe Thr Leu Met Val
                    260                 265                 270
Ala Gly Glu Ser Gly Leu Gly Lys Ser Thr Leu Val Asn Ser Leu Phe
                    275                 280                 285
Leu Thr Asp Leu Tyr Arg Asp Arg Lys Leu Leu Gly Ala Glu Glu Arg
                    290                 295                 300
Ile Met Gln Thr Val Glu Ile Thr Lys His Ala Val Asp Ile Glu Lys
305                 310                 315                 320
Lys Gly Val Arg Leu Arg Leu Thr Ile Val Asp Thr Pro Ser Phe Gly
                    325                 330                 335
Asp Ala Val Asn Asn Thr Glu Cys Met Ser Asp Trp Lys Pro Val Ala
                    340                 345                 350
Glu Tyr Ile Asp Gln Gln Phe Glu Gln Tyr Phe Arg Asp Glu Ser Gly
                    355                 360                 365
Leu Asn Arg Lys Asn Ile Gln Asp Asn Arg Val His Cys Cys Leu Tyr
                    370                 375                 380
Phe Ile Ser Pro Phe Gly His Gly Leu Arg Pro Leu Asp Val Glu Phe
385                 390                 395                 400
Met Lys Ala Leu His Gln Arg Val Asn Ile Val Pro Ile Leu Ala Lys
                    405                 410                 415
Ala Asp Thr Leu Thr Pro Pro Glu Val Asp His Lys Lys Arg Lys Ile
                    420                 425                 430
Arg Glu Glu Ile Glu His Phe Gly Ile Lys Ile Tyr Gln Phe Pro Asp
                    435                 440                 445
Cys Asp Ser Asp Glu Asp Glu Asp Phe Lys Leu Gln Asp Gln Ala Leu
                    450                 455                 460
Lys Glu Ser Ile Pro Phe Ala Val Ile Gly Ser Asn Thr Val Val Glu
465                 470                 475                 480
Ala Arg Gly Arg Arg Val Arg Gly Arg Leu Tyr Pro Trp Gly Ile Val
                    485                 490                 495
Glu Val Glu Asn Pro Gly His Cys Asp Phe Val Lys Leu Arg Thr Met
                    500                 505                 510
Leu Val Arg Thr His Met Gln Asp Leu Lys Asp Val Thr Arg Glu Thr
                    515                 520                 525
His Tyr Glu Asn Tyr Arg Ala Gln Cys Ile Gln Ser Met Thr Arg Leu
                    530                 535                 540
Val Val Asn Glu Arg Asn Arg Lys Tyr Asp Gln Lys Pro Gly Gln Ser
545                 550                 555                 560
Trp Gln Gly Glu Ile Pro Ser Leu Ala Leu Gly Glu Thr Lys Pro Tyr
                    565                 570                 575
Phe Cys Ser Ser Ile Gly Pro Gly Leu Asn Leu Ser Gly Cys Trp Gly
                    580                 585                 590
Pro Pro Arg Leu Ile Asn Pro Phe Leu Pro Leu Ala Asn
                    595                 600                 605

SEQ ID NO:3 gaaaggagca agccaggaag ccagacaaca acagcatcaa acaaggctg tttctgtgtg     60 tgaggaactt tgcctgggag ataaaattag acctagagct ttctgacagg gagtctgaag   120
cgtgggacat ggaccgttca ctgggatggc aagggaattc tgtccctgag acaggactg    180 aagctgggat caagcgtttc ctggaggaca ccacggatga tggagaactg agcaagttcg   240
```

-continued

```
tgaaggattt ctcaggaaat gcgagctgcc acccaccaga ggctaagacc tgggcatcca  300
ggccccaagt cccggagcca aggccccagg ccccggacct ctatgatgat gacctggagt  360
tcagaccccc ctcgcggccc cagtcctctg acaaccagca gtacttctgt gccccagccc  420
ctctcagccc atctgccagg ccccgcagcc catggggcaa gcttgatccc tatgattcct  480
ctgaggatga caaggagtat gtgggctttg caaccctccc caaccaagtc caccgaaagt  540
ccgtgaagaa aggctttgac tttacccctca tggtggcagg agagtctggc ctgggcaaat  600
ccacacttgt caatagcctc ttcctcactg atctgtaccg ggaccggaaa cttcttggtg  660
ctgaagagag gatcatgcaa actgtggaga tcactaagca tgcagtggac atagaagaga  720
agggtgtgag gctgcggctc accattgtgg acacaccagg ttttggggat gcagtcaaca  780
acacagagtg ctggaagcct gtggcagaat acattgatca gcagtttgag cagtatttcc  840
gagacgagag tggcctgaac cgaaagaaca tccaagacaa cagggtgcac tgctgcctgt  900
acttcatctc acccttcggc catgggctcc ggccattgga tgttgaattc atgaaggccc  960
tgcatcagcg ggtcaacatc gtgcctatcc tggctaaggc agacacactg acacctcccg 1020
aagtggacca caagaaacgc aaaatccggg aggagattga gcattttgga atcaagatct 1080
atcaattccc agactgtgac tctgatgagg atgaggactt caaattgcag gaccaagccc 1140
taaaggaaag catcccattt gcagtaattg gcagcaacac tgtagtagag gccagagggc 1200
ggcgagttcg gggtcgactc tacccctggg gcatcgtgga agtggaaaac ccagggcact 1260
gcgactttgt gaagctgagg acaatgctgg tacgtaccca catgcaggac ctgaaggatg 1320
tgacacggga gacacattat gagaactacc gggcacagtg catccagagc atgacccgcc 1380
tggtggtgaa ggaacggaat cgcaacaaac tgactcggga agtggtacc gacttcccca 1440
tccctgctgt cccaccaggg acagatccag aaactgagaa gcttatccga gagaaagatg 1500
aggagctgcg gcggatgcag gagatgctac acaaaataca aaaacagatg aaggagaact 1560
attaactggc tttcagccct ggatatttaa atctcctcct cttcttcctg tccatgccgg 1620
cccctcccag caccagctct gctcaggccc cttcagctac tgccacttcg cctaacatcc 1680
ctgctgactg cccagagact cagaggaaat aaagtttaat aaatctgtag gtggc         1735
```

SEQ ID NO:4

```
Met Asp Arg Ser Leu Gly Trp Gln Gly Asn Ser Val Pro Glu Asp Arg
 1               5                  10                  15
Thr Glu Ala Gly Ile Lys Arg Phe Leu Glu Asp Thr Thr Asp Asp Gly
                20                  25                  30
Glu Leu Ser Lys Phe Val Lys Asp Phe Ser Gly Asn Ala Ser Cys His
                35                  40                  45
Pro Pro Glu Ala Lys Thr Trp Ala Ser Arg Pro Gln Val Pro Glu Pro
        50                  55                  60
Arg Pro Gln Ala Pro Asp Leu Tyr Asp Asp Asp Leu Glu Phe Arg Pro
65                  70                  75                  80
Pro Ser Arg Pro Gln Ser Ser Asp Asn Gln Gln Tyr Phe Cys Ala Pro
                85                  90                  95
Ala Pro Leu Ser Pro Ser Ala Arg Pro Arg Ser Pro Trp Gly Lys Leu
                100                 105                 110
Asp Pro Tyr Asp Ser Ser Glu Asp Asp Lys Glu Tyr Val Gly Phe Ala
        115                 120                 125
Thr Leu Pro Asn Gln Val His Arg Lys Ser Val Lys Lys Gly Phe Asp
    130                 135                 140
```

```
                              -continued
Phe Thr Leu Met Val Ala Gly Glu Ser Gly Leu Gly Lys Ser Thr Leu
145                 150                 155                 160

Val Asn Ser Leu Phe Leu Thr Asp Leu Tyr Arg Asp Arg Lys Leu Leu
                165                 170                 175

Gly Ala Glu Glu Arg Ile Met Gln Thr Val Glu Ile Thr Lys His Ala
            180                 185                 190

Val Asp Ile Glu Glu Lys Gly Val Arg Leu Arg Leu Thr Ile Val Asp
        195                 200                 205

Thr Pro Gly Phe Gly Asp Ala Val Asn Asn Thr Glu Cys Val Lys Pro
    210                 215                 220

Val Ala Glu Tyr Ile Asp Gln Gln Phe Glu Gln Tyr Phe Arg Asp Glu
225                 230                 235                 240

Ser Gly Leu Asn Arg Lys Asn Ile Gln Asp Asn Arg Val His Cys Cys
                245                 250                 255

Leu Tyr Phe Ile Ser Pro Phe Gly His Gly Leu Arg Pro Leu Asp Val
            260                 265                 270

Glu Phe Met Lys Ala Leu His Gln Arg Val Asn Ile Val Pro Ile Leu
        275                 280                 285

Ala Lys Ala Asp Thr Leu Thr Pro Pro Glu Val Asp His Lys Lys Arg
    290                 295                 300

Lys Ile Arg Glu Glu Ile Glu His Phe Gly Ile Lys Ile Tyr Gln Phe
305                 310                 315                 320

Pro Asp Cys Asp Ser Asp Glu Asp Glu Asp Phe Lys Leu Gln Asp Gln
                325                 330                 335

Ala Leu Lys Glu Ser Ile Pro Phe Ala Val Ile Gly Ser Asn Thr Val
            340                 345                 350

Val Glu Ala Arg Gly Arg Arg Val Arg Gly Arg Leu Tyr Pro Trp Gly
        355                 360                 365

Ile Val Glu Val Glu Asn Pro Gly His Cys Asp Phe Val Lys Leu Arg
    370                 375                 380

Thr Met Leu Val Arg Thr His Met Gln Asp Leu Lys Asp Val Thr Arg
385                 390                 395                 400

Glu Thr His Tyr Glu Asn Tyr Arg Ala Gln Cys Ile Gln Ser Met Thr
                405                 410                 415

Arg Leu Val Val Lys Glu Arg Asn Arg Asn Lys Leu Thr Arg Glu Ser
            420                 425                 430

Gly Thr Asp Phe Pro Ile Pro Ala Val Pro Pro Gly Thr Asp Pro Glu
        435                 440                 445

Thr Glu Lys Leu Ile Arg Glu Lys Asp Glu Glu Leu Arg Arg Met Asp
    450                 455                 460

Glu Met Leu His Lys Ile Gln Lys Gln Met Lys Glu Asn Tyr
465                 470                 475
```

What is claimed is:

1. A method for detecting human colorectal cancer, wherein the method comprises the steps of:

bringing a specimen from a pathologic tissue of a patient into contact with an isolated polynucleotide having at least 97% homology with DNA encoding a bradeion protein which comprises an amino acid sequence 1–119 of SEQ ID NO:4 and which has the following properties:

(i) it is a transmembranous protein;

(ii) it has a transmembrane portion, an extracellular portion, and a cytoplasmic portion in its molecule as determined by a hydrophobicity analysis according to Kyte-Doolittle method;

(iii) it is expressed in the human adult normal brain and heart, the expression level thereof in the heart being about 10% or lower of that in the brain, while it is not expressed in other adult normal organs of spleen, lung, liver, skeletal muscle, kidney and pancreas, and in fetal brain, lung, heart and kidney;

(iv) it induces programmed cell death when overexpressed in a cultured human brain-derived undifferentiated nerve cell line;

(v) it induces termination of cell division and aging when overexpressed in a cultured human brain-derived differentiated nerve cell;

(vi) it is located in cytoplasm in the course of the induced cell death, and forms an intracellular aggregate when overexpressed; and (vii) it is expressed in a human colorectal cancer cell line or in a human malignant melanoma cell line, but not in leukemia, lymphoma and lung carcinoma;

or a DNA fragment with at least 15 nucleotides encoding a fragment of said bradeion protein, or complements thereof;

detecting the presence of a nucleic acid encoding said bradeion protein in said specimen; and determining whether there exists said cancer in said patient by using the presence of said nucleic acid as an indication.

2. The method of claim 1, wherein said DNA is cDNA for bradeion protein, which is contained in a deposited plasmid, the accession number FERM BP-6922.

3. The method of claim 1, wherein said DNA is cDNA, which encodes a bradeion protein having an amino acid sequence of SEQ ID NO:2 or 4.

4. The method of claim 1, wherein said DNA is cDNA for bradeion protein having the nucleotide sequence 129–1943 of SEQ ID NO:1 or the nucleotide sequence 129–1562 of SEQ ID NO: 3.

5. A method of claim 1, wherein said detection is conducted by hybridization or RT-PCR.

6. The method of claim 1 wherein said DNA, DNA fragment or complements thereof is/are labeled.

7. The method for detecting human colorectal cancer, wherein the method comprises the steps of:

bringing a specimen from a pathologic tissue of a patient into contact with an antibody which is immunologically reactive with a bradeion protein which comprises an amino acid sequence having at least 97% homology to the amino acid sequence 1–119 of SEQ ID NO:4 and which has the following properties:

(i) it is a transmembranous protein;

(ii) it has a transmembrane portion, an extracellular portion, and a cytoplasmic portion in its molecule as determined by a hydrophobicity analysis according to Kyte-Doolittle method;

(iii) it is expressed in the human adult normal brain and heart, the expression level thereof in the heart being about 10% or lower of that in the brain, while it is not expressed in other adult normal organs of spleen, lung, liver, skeletal muscle, kidney and pancreas, and in fetal brain, lung, heart and kidney;

(iv) it induces programmed cell death when overexpressed in a cultured human brain-derived undifferentiated nerve cell line;

(v) it induces termination of cell division and aging when overexpressed in a cultured human brain-derived differentiated nerve cell;

(vi) it is located in cytoplasm in the course of the induced cell death, and forms an intracellular aggregate when overexpressed; and (vii) it is expressed in a human colorectal cancer cell line or in a human malignant melanoma cell line, but not in leukemia, lymphoma and lung carcinoma;

detecting the presence of said bradeion protein in said specimen; and determining whether there exists said cancer in said patient by using the presence of said bradeion protein as an indication.

8. The method of claim 7, wherein said antibody is elicited against a bradeion protein encoded by cDNA which is contained in a deposited plasmid, the accession number FERM BP-6922.

9. The method of claim 7, wherein said antibody is elicited against a bradeion protein having an amino acid sequence of SEQ ID NO:2 or 4.

10. A method of claim 7, wherein said detection is conducted by an immunoassay including enzymatic immunoassay, radioimmunoassay, or fluorescent antibody method.

11. A method of claim 7, wherein said antibody is monoclonal.

12. A method of claim 7, wherein said antibody is polyclonal.

13. A method for detecting human malignant melanoma, wherein the method comprises the steps of:

bringing a specimen from a pathologic tissue of a patient into contact with DNA encoding a bradeion protein, the DNA being contained in a deposited plasmid, the accession number FERM BP-6922, or the complement thereof;

detecting the presence of a nucleic acid encoding said bradeion protein in said specimen; and determining whether there exists said cancer in said patient by using the presence of said nucleic acid as an indication.

14. A method for detecting human malignant melanoma, wherein the method comprises the steps of:
bringing a specimen from a pathologic tissue of a patient into contact with DNA encoding a bradeion protein having the nucleotide sequence 129–1943 of SEQ ID NO:1;
detecting the presence of a nucleic acid encoding said bradeion protein in said specimen; and
determining whether there exists said cancer in said patient by using the presence of said nucleic acid as an indication.

15. A method of claim 13, wherein said detection is conducted by hybridization.

16. A method of claim 13, wherein said DNA is labeled.

17. A method of claim 14, wherein said detection is conducted by hybridization.

18. A method of claim 14, wherein said DNA is labeled.

* * * * *

SEQUENCE LISTING

<160> NUMBER OF SEQ ID NOS: 6

<210> SEQ ID NO 1
<211> LENGTH: 2274
<212> TYPE: DNA
<213> ORGANISM: Homo sapiens
<220> FEATURE:
<221> NAME/KEY: CDS
<222> LOCATION: (129)..(1943)

<400> SEQUENCE: 1

```
gaaaggagca agccaggaag ccagacaaca acagcatcaa acaaggctg tttctgtgtg      60 tgaggaactt tgcctgggag ataaaattag acctagagct ttctgacagg gagtctgaag    120 cgtgggac atg gac cgt tca ctg gga tgg caa ggg aat tct gtc cct gag    170
         Met Asp Arg Ser Leu Gly Trp Gln Gly Asn Ser Val Pro Glu
          1               5                  10 gac agg act gaa cct ggg atc aac cgt ttc ctg gag gac acc acg gat    218
Asp Arg Thr Glu Pro Gly Ile Asn Arg Phe Leu Glu Asp Thr Thr Asp
 15              20                  25                  30 gat gga gaa ctg agc aag ttc gtg aag gat ttc tca gga aat gcg agc    266
Asp Gly Glu Leu Ser Lys Phe Val Lys Asp Phe Ser Gly Asn Ala Ser
                 35                  40                  45 tgc cac cca cca gag gct aag acc tgg gca tcc agg ccc caa gtc ccg    314
Cys His Pro Pro Glu Ala Lys Thr Trp Ala Ser Arg Pro Gln Val Pro
             50                  55                  60 gag cca agg ccc cag gcc ccg gac ctc tat gat gat gac ctg gag ttc    362
Glu Pro Arg Pro Gln Ala Pro Asp Leu Tyr Asp Asp Asp Leu Glu Phe
         65                  70                  75 aga ccc ccc tcg cgg ccc cag tcc tct gac aac cag cag tac ttc tgt    410
Arg Pro Pro Ser Arg Pro Gln Ser Ser Asp Asn Gln Gln Tyr Phe Cys
 80                  85                  90 gcc cca gcc cct ctc agc cca tct gcc agg ccc cgc agc cca tgg ggg    458
Ala Pro Ala Pro Leu Ser Pro Ser Ala Arg Pro Arg Ser Pro Trp Gly
 95                 100                 105                 110 gag ctt gat ccc tat gat tcc tct gag gta gag cct cca gcc ctg cct    506
Glu Leu Asp Pro Tyr Asp Ser Ser Glu Val Glu Pro Pro Ala Leu Pro
                115                 120                 125 ttg cct ttc agt ggg ctg ctg cag gaa gac cgg ggg cag gga gca gga    554
Leu Pro Phe Ser Gly Leu Leu Gln Glu Asp Arg Gly Gln Gly Ala Gly
            130                 135                 140 atg tgt gtg tgt gtg tgt gtg tgt gtg tgt tgt gtg ttt gtg tgt       602
Met Cys Val Cys Val Cys Val Cys Val Cys Val Cys Val Phe Val Cys
                145                 150                 155 gtg tgt atc tgg gac cca ttt cag tcc tgt gtc agc cct agc tcc aaa    650
Val Cys Ile Trp Asp Pro Phe Gln Ser Cys Val Ser Pro Ser Ser Lys
    160                 165                 170 ata tct gcc ccc aag ggc act gga aat ttg cag ttt cag caa ggg cag    698
Ile Ser Ala Pro Lys Gly Thr Gly Asn Leu Gln Phe Gln Gln Gly Gln
175                 180                 185                 190 gag gcc cag ctg gtg gcc tca gat ggg aac tca cag aag tct ggc act    746
Glu Ala Gln Leu Val Ala Ser Asp Gly Asn Ser Gln Lys Ser Gly Thr
                195                 200                 205 gct ttt tta agg ctg ggg caa agg cct gaa agg gag aga aga ttg gcg    794
Ala Phe Leu Arg Leu Gly Gln Arg Pro Glu Arg Glu Arg Arg Leu Ala
            210                 215                 220 ctg ggt gcc ggg gcc cct ttg gct cct cac cgt gat gca ttc tgc ctt    842
Leu Gly Ala Gly Ala Pro Leu Ala Pro His Arg Asp Ala Phe Cys Leu
        225                 230                 235 cct gtc tac tac gat gac aag gag tat gtg ggc ttt gca acc ctc ccc    890
Pro Val Tyr Tyr Asp Asp Lys Glu Tyr Val Gly Phe Ala Thr Leu Pro
        240                 245                 250 aac caa gtc cac cga aag tcc gtg aag aaa ggc ttt gac ttt acc ctc    938
Asn Gln Val His Arg Lys Ser Val Lys Lys Gly Phe Asp Phe Thr Leu
255                 260                 265                 270 atg gtg gca gga gag tct ggc ctg ggc aaa tcc aca ctt gtc aat agc    986
Met Val Ala Gly Glu Ser Gly Leu Gly Lys Ser Thr Leu Val Asn Ser
            275                 280                 285 ctc ttc ctc act gat ctg tac cgg gac cgg aaa ctt ctt ggt gct gaa   1034
```

```
                                                                -continued

Leu Phe Leu Thr Asp Leu Tyr Arg Asp Arg Lys Leu Leu Gly Ala Glu
            290                 295                 300 gaa agg atc atg caa act gtg gag atc act aag cat gca gtg gac ata    1082
Glu Arg Ile Met Gln Thr Val Glu Ile Thr Lys His Ala Val Asp Ile
            305                 310                 315 gaa aaa aaa ggt gtg agg ctg cgg ctc acc att gtg gac aca cca agt    1130
Glu Lys Lys Gly Val Arg Leu Arg Leu Thr Ile Val Asp Thr Pro Ser
320                 325                 330 ttt ggg gat gca gtc aac aac aca gag tgt atg tct gac tgg aag cct    1178
Phe Gly Asp Ala Val Asn Asn Thr Glu Cys Met Ser Asp Trp Lys Pro
335                 340                 345                 350 gtg gca gaa tac att gat cag cag ttt gag cag tat ttc cga gac gag    1226
Val Ala Glu Tyr Ile Asp Gln Gln Phe Glu Gln Tyr Phe Arg Asp Glu
            355                 360                 365 agt ggc ctg aac cga aag aac atc caa gac aac agg gtg cac tgc tgc    1274
Ser Gly Leu Asn Arg Lys Asn Ile Gln Asp Asn Arg Val His Cys Cys
            370                 375                 380 ctg tac ttc atc tca ccc ttc ggc cat ggg ctc cgg cca ttg gat gtt    1322
Leu Tyr Phe Ile Ser Pro Phe Gly His Gly Leu Arg Pro Leu Asp Val
            385                 390                 395 gaa ttc atg aag gcc ctg cat cag cgg gtc aac atc gtg cct atc ctg    1370
Glu Phe Met Lys Ala Leu His Gln Arg Val Asn Ile Val Pro Ile Leu
    400                 405                 410 gct aag gca gac aca ctg aca cct ccc gaa gtg gac cac aag aaa cgc    1418
Ala Lys Ala Asp Thr Leu Thr Pro Pro Glu Val Asp His Lys Lys Arg
415                 420                 425                 430 aaa atc cgg gag gag att gag cat ttt gga atc aag atc tat caa ttc    1466
Lys Ile Arg Glu Glu Ile Glu His Phe Gly Ile Lys Ile Tyr Gln Phe
            435                 440                 445 cca gac tgt gac tct gat gag gat gag gac ttc aaa ttg cag gac caa    1514
Pro Asp Cys Asp Ser Asp Glu Asp Glu Asp Phe Lys Leu Gln Asp Gln
            450                 455                 460 gcc cta aag gaa agc atc cca ttt gca gta att ggc agc aac act gta    1562
Ala Leu Lys Glu Ser Ile Pro Phe Ala Val Ile Gly Ser Asn Thr Val
            465                 470                 475 gta gag gcc aga ggg cgg cga gtt cgg ggt cga ctc tac ccc tgg ggc    1610
Val Glu Ala Arg Gly Arg Arg Val Arg Gly Arg Leu Tyr Pro Trp Gly
            480                 485                 490 atc gtg gaa gtg gaa aac cca ggg cac tgc gac ttt gtg aag ctg agg    1658
Ile Val Glu Val Glu Asn Pro Gly His Cys Asp Phe Val Lys Leu Arg
495                 500                 505                 510 aca atg ctg gta cgt acc cac atg cag gac ctg aag gat gtg aca cgg    1706
Thr Met Leu Val Arg Thr His Met Gln Asp Leu Lys Asp Val Thr Arg
            515                 520                 525 gag aca cat tat gag aac tac cgg gca cag tgc atc cag agc atg acc    1754
Glu Thr His Tyr Glu Asn Tyr Arg Ala Gln Cys Ile Gln Ser Met Thr
            530                 535                 540 cgc ctg gtg gtg aat gaa cgg aat cgc aag tat gac cag aag cca gga    1802
Arg Leu Val Val Asn Glu Arg Asn Arg Lys Tyr Asp Gln Lys Pro Gly
            545                 550                 555 caa agc tgg cag ggg gag atc cca agc cta gcc ttg ggt gag acc aag    1850
Gln Ser Trp Gln Gly Glu Ile Pro Ser Leu Ala Leu Gly Glu Thr Lys
            560                 565                 570 ccc tac ttt tgt tct tct ata ggc cct ggg ctc aat cta agc ggg tgc    1898
Pro Tyr Phe Cys Ser Ser Ile Gly Pro Gly Leu Asn Leu Ser Gly Cys
575                 580                 585                 590 tgg ggt cct cct cgc ctt atc aac cct ttt ctc cct tta gca aac        1943
Trp Gly Pro Pro Arg Leu Ile Asn Pro Phe Leu Pro Leu Ala Asn
            595                 600                 605
```

-continued

```
tgactcggga aagtggtacc gacttcccca tccctgctgt cccaccaggg acagatccag    2003
aaactgagaa gcttatccca gagaaagatt aggagctgcg gcggatacac gagatactac    2063
accaaatacc aaaacagata aaggagaact atttactggc tttcagccct ggatatttaa    2123
atctcctcct cttcttcctg tccatgccgg ccctcccag caccagctct gctcaggccc     2183
cttcagctac tgccacttcg ccttacatcc ctgctgactg cccagagact cagaggaaat    2243
aaagtttaat aaatctgtag gtggcttctg g                                   2274
```

<210> SEQ ID NO 2
<211> LENGTH: 605
<212> TYPE: PRT
<213> ORGANISM: Homo sapiens

<400> SEQUENCE: 2

```
Met Asp Arg Ser Leu Gly Trp Gln Gly Asn Ser Val Pro Glu Asp Arg
 1               5                  10                  15

Thr Glu Pro Gly Ile Asn Arg Phe Leu Glu Asp Thr Thr Asp Asp Gly
            20                  25                  30

Glu Leu Ser Lys Phe Val Lys Asp Phe Ser Gly Asn Ala Ser Cys His
        35                  40                  45

Pro Pro Glu Ala Lys Thr Trp Ala Ser Arg Pro Gln Val Pro Glu Pro
    50                  55                  60

Arg Pro Gln Ala Pro Asp Leu Tyr Asp Asp Leu Glu Phe Arg Pro
65                  70                  75                  80

Pro Ser Arg Pro Gln Ser Ser Asp Asn Gln Gln Tyr Phe Cys Ala Pro
                85                  90                  95

Ala Pro Leu Ser Pro Ser Ala Arg Pro Arg Ser Pro Trp Gly Glu Leu
            100                 105                 110

Asp Pro Tyr Asp Ser Ser Glu Val Glu Pro Pro Ala Leu Pro Leu Pro
        115                 120                 125

Phe Ser Gly Leu Leu Gln Glu Asp Arg Gly Gln Gly Ala Gly Met Cys
    130                 135                 140

Val Cys Val Cys Val Cys Val Cys Val Phe Val Cys Val Cys
145                 150                 155                 160

Ile Trp Asp Pro Phe Gln Ser Cys Val Ser Pro Ser Lys Ile Ser
                165                 170                 175

Ala Pro Lys Gly Thr Gly Asn Leu Gln Phe Gln Gln Gly Gln Glu Ala
            180                 185                 190

Gln Leu Val Ala Ser Asp Gly Asn Ser Gln Lys Ser Gly Thr Ala Phe
        195                 200                 205

Leu Arg Leu Gly Gln Arg Pro Glu Arg Glu Arg Leu Ala Leu Gly
    210                 215                 220

Ala Gly Ala Pro Leu Ala Pro His Arg Asp Ala Phe Cys Leu Pro Val
225                 230                 235                 240

Tyr Tyr Asp Asp Lys Glu Tyr Val Gly Phe Ala Thr Leu Pro Asn Gln
                245                 250                 255

Val His Arg Lys Ser Val Lys Lys Gly Phe Asp Phe Thr Leu Met Val
            260                 265                 270

Ala Gly Glu Ser Gly Leu Gly Lys Ser Thr Leu Val Asn Ser Leu Phe
        275                 280                 285

Leu Thr Asp Leu Tyr Arg Asp Arg Lys Leu Leu Gly Ala Glu Glu Arg
    290                 295                 300

Ile Met Gln Thr Val Glu Ile Thr Lys His Ala Val Asp Ile Glu Lys
305                 310                 315                 320
```

-continued

```
Lys Gly Val Arg Leu Arg Leu Thr Ile Val Asp Thr Pro Ser Phe Gly
            325                 330                 335
Asp Ala Val Asn Asn Thr Glu Cys Met Ser Asp Trp Lys Pro Val Ala
            340                 345                 350
Glu Tyr Ile Asp Gln Gln Phe Glu Gln Tyr Phe Arg Asp Glu Ser Gly
            355                 360                 365
Leu Asn Arg Lys Asn Ile Gln Asp Asn Arg Val His Cys Cys Leu Tyr
            370                 375             380
Phe Ile Ser Pro Phe Gly His Gly Leu Arg Pro Leu Asp Val Glu Phe
385                 390                 395                 400
Met Lys Ala Leu His Gln Arg Val Asn Ile Val Pro Ile Leu Ala Lys
            405                 410                 415
Ala Asp Thr Leu Thr Pro Pro Glu Val Asp His Lys Lys Arg Lys Ile
            420                 425                 430
Arg Glu Glu Ile Glu His Phe Gly Ile Lys Ile Tyr Gln Phe Pro Asp
            435                 440                 445
Cys Asp Ser Asp Glu Asp Glu Asp Phe Lys Leu Gln Asp Gln Ala Leu
            450                 455                 460
Lys Glu Ser Ile Pro Phe Ala Val Ile Gly Ser Asn Thr Val Val Glu
465                 470                 475                 480
Ala Arg Gly Arg Arg Val Arg Gly Arg Leu Tyr Pro Trp Gly Ile Val
            485                 490                 495
Glu Val Glu Asn Pro Gly His Cys Asp Phe Val Lys Leu Arg Thr Met
            500                 505                 510
Leu Val Arg Thr His Met Gln Asp Leu Lys Asp Val Thr Arg Glu Thr
            515                 520                 525
His Tyr Glu Asn Tyr Arg Ala Gln Cys Ile Gln Ser Met Thr Arg Leu
            530                 535                 540
Val Val Asn Glu Arg Asn Arg Lys Tyr Asp Gln Lys Pro Gly Gln Ser
545                 550                 555                 560
Trp Gln Gly Glu Ile Pro Ser Leu Ala Leu Gly Glu Thr Lys Pro Tyr
            565                 570                 575
Phe Cys Ser Ser Ile Gly Pro Gly Leu Asn Leu Ser Gly Cys Trp Gly
            580                 585                 590
Pro Pro Arg Leu Ile Asn Pro Phe Leu Pro Leu Ala Asn
            595                 600                 605

<210> SEQ ID NO 3
<211> LENGTH: 1735
<212> TYPE: DNA
<213> ORGANISM: Homo sapiens
<220> FEATURE:
<221> NAME/KEY: CDS
<222> LOCATION: (129)..(1562)

<400> SEQUENCE: 3
gaaaggagca agccaggaag ccagacaaca acagcatcaa acaaggctg tttctgtgtg      60 tgaggaactt tgcctgggag ataaaattag acctagagct ttctgacagg gagtctgaag    120 cgtgggac atg gac cgt tca ctg gga tgg caa ggg aat tct gtc cct gag    170
         Met Asp Arg Ser Leu Gly Trp Gln Gly Asn Ser Val Pro Glu
           1               5                  10 gac agg act gaa gct ggg atc aag cgt ttc ctg gag gac acc acg gat    218
Asp Arg Thr Glu Ala Gly Ile Lys Arg Phe Leu Glu Asp Thr Thr Asp
 15                  20                  25                  30 gat gga gaa ctg agc aag ttc gtg aag gat ttc tca gga aat gcg agc    266
```

```
                    -continued

Asp Gly Glu Leu Ser Lys Phe Val Lys Asp Phe Ser Gly Asn Ala Ser
                 35                  40                  45 tgc cac cca cca gag gct aag acc tgg gca tcc agg ccc caa gtc ccg      314
Cys His Pro Pro Glu Ala Lys Thr Trp Ala Ser Arg Pro Gln Val Pro
             50                  55                  60 gag cca agg ccc cag gcc ccg gac ctc tat gat gat gac ctg gag ttc      362
Glu Pro Arg Pro Gln Ala Pro Asp Leu Tyr Asp Asp Asp Leu Glu Phe
         65                  70                  75 aga ccc ccc tcg cgg ccc cag tcc tct gac aac cag cag tac ttc tgt      410
Arg Pro Pro Ser Arg Pro Gln Ser Ser Asp Asn Gln Gln Tyr Phe Cys
     80                  85                  90 gcc cca gcc cct ctc agc cca tct gcc agg ccc cgc agc cca tgg ggc      458
Ala Pro Ala Pro Leu Ser Pro Ser Ala Arg Pro Arg Ser Pro Trp Gly
 95                 100                 105                 110 aag ctt gat ccc tat gat tcc tct gag gat gac aag gag tat gtg ggc      506
Lys Leu Asp Pro Tyr Asp Ser Ser Glu Asp Asp Lys Glu Tyr Val Gly
                115                 120                 125 ttt gca acc ctc ccc aac caa gtc cac cga aag tcc gtg aag aaa ggc      554
Phe Ala Thr Leu Pro Asn Gln Val His Arg Lys Ser Val Lys Lys Gly
            130                 135                 140 ttt gac ttt acc ctc atg gtg gca gga gag tct ggc ctg ggc aaa tcc      602
Phe Asp Phe Thr Leu Met Val Ala Gly Glu Ser Gly Leu Gly Lys Ser
            145                 150                 155 aca ctt gtc aat agc ctc ttc ctc act gat ctg tac cgg gac cgg aaa      650
Thr Leu Val Asn Ser Leu Phe Leu Thr Asp Leu Tyr Arg Asp Arg Lys
        160                 165                 170 ctt ctt ggt gct gaa gag agg atc atg caa act gtg gag atc act aag      698
Leu Leu Gly Ala Glu Glu Arg Ile Met Gln Thr Val Glu Ile Thr Lys
175                 180                 185                 190 cat gca gtg gac ata gaa gag aag ggt gtg agg ctg cgg ctc acc att      746
His Ala Val Asp Ile Glu Glu Lys Gly Val Arg Leu Arg Leu Thr Ile
                195                 200                 205 gtg gac aca cca ggt ttt ggg gat gca gtc aac aac aca gag tgc tgg      794
Val Asp Thr Pro Gly Phe Gly Asp Ala Val Asn Asn Thr Glu Cys Trp
            210                 215                 220 aag cct gtg gca gaa tac att gat cag cag ttt gag cag tat ttc cga      842
Lys Pro Val Ala Glu Tyr Ile Asp Gln Gln Phe Glu Gln Tyr Phe Arg
            225                 230                 235 gac gag agt ggc ctg aac cga aag aac atc caa gac aac agg gtg cac      890
Asp Glu Ser Gly Leu Asn Arg Lys Asn Ile Gln Asp Asn Arg Val His
        240                 245                 250 tgc tgc ctg tac ttc atc tca ccc ttc ggc cat ggg ctc cgg cca ttg      938
Cys Cys Leu Tyr Phe Ile Ser Pro Phe Gly His Gly Leu Arg Pro Leu
255                 260                 265                 270 gat gtt gaa ttc atg aag gcc ctg cat cag cgg gtc aac atc gtg cct      986
Asp Val Glu Phe Met Lys Ala Leu His Gln Arg Val Asn Ile Val Pro
                275                 280                 285 atc ctg gct aag gca gac aca ctg aca cct ccc gaa gtg gac cac aag     1034
Ile Leu Ala Lys Ala Asp Thr Leu Thr Pro Pro Glu Val Asp His Lys
            290                 295                 300 aaa cgc aaa atc cgg gag gag att gag cat ttt gga atc aag atc tat     1082
Lys Arg Lys Ile Arg Glu Glu Ile Glu His Phe Gly Ile Lys Ile Tyr
        305                 310                 315 caa ttc cca gac tgt gac tct gat gag gat gag gac ttc aaa ttg cag     1130
Gln Phe Pro Asp Cys Asp Ser Asp Glu Asp Glu Asp Phe Lys Leu Gln
    320                 325                 330 gac caa gcc cta aag gaa agc atc cca ttt gca gta att ggc agc aac     1178
Asp Gln Ala Leu Lys Glu Ser Ile Pro Phe Ala Val Ile Gly Ser Asn
335                 340                 345                 350
```

-continued

```
act gta gta gag gcc aga ggg cgg cga gtt cgg ggt cga ctc tac ccc    1226
Thr Val Val Glu Ala Arg Gly Arg Arg Val Arg Gly Arg Leu Tyr Pro
            355                 360                 365 tgg ggc atc gtg gaa gtg gaa aac cca ggg cac tgc gac ttt gtg aag    1274
Trp Gly Ile Val Glu Val Glu Asn Pro Gly His Cys Asp Phe Val Lys
370                 375                 380 ctg agg aca atg ctg gta cgt acc cac atg cag gac ctg aag gat gtg    1322
Leu Arg Thr Met Leu Val Arg Thr His Met Gln Asp Leu Lys Asp Val
    385                 390                 395 aca cgg gag aca cat tat gag aac tac cgg gca cag tgc atc cag agc    1370
Thr Arg Glu Thr His Tyr Glu Asn Tyr Arg Ala Gln Cys Ile Gln Ser
400                 405                 410 atg acc cgc ctg gtg gtg aag gaa cgg aat cgc aac aaa ctg act cgg    1418
Met Thr Arg Leu Val Val Lys Glu Arg Asn Arg Asn Lys Leu Thr Arg
415                 420                 425                 430 gaa agt ggt acc gac ttc ccc atc cct gct gtc cca cca ggg aca gat    1466
Glu Ser Gly Thr Asp Phe Pro Ile Pro Ala Val Pro Pro Gly Thr Asp
                435                 440                 445 cca gaa act gag aag ctt atc cga gag aaa gat gag gag ctg cgg cgg    1514
Pro Glu Thr Glu Lys Leu Ile Arg Glu Lys Asp Glu Glu Leu Arg Arg
            450                 455                 460 atg cag gag atg cta cac aaa ata caa aaa cag atg aag gag aac tat    1562
Met Gln Glu Met Leu His Lys Ile Gln Lys Gln Met Lys Glu Asn Tyr
465                 470                 475 taactggctt tcagccctgg atatttaaat ctcctcctct tcttcctgtc catgccggcc    1622
cctcccagca ccagctctgc tcaggcccct tcagctactg ccacttcgcc taacatccct    1682
gctgactgcc cagagactca gaggaaataa agtttaataa atctgtaggt ggc          1735

<210> SEQ ID NO 4
<211> LENGTH: 478
<212> TYPE: PRT
<213> ORGANISM: Homo sapiens

<400> SEQUENCE: 4

Met Asp Arg Ser Leu Gly Trp Gln Gly Asn Ser Val Pro Glu Asp Arg
 1               5                  10                  15

Thr Glu Ala Gly Ile Lys Arg Phe Leu Glu Asp Thr Thr Asp Asp Gly
            20                  25                  30

Glu Leu Ser Lys Phe Val Lys Asp Phe Ser Gly Asn Ala Ser Cys His
        35                  40                  45

Pro Pro Glu Ala Lys Thr Trp Ala Ser Arg Pro Gln Val Pro Glu Pro
    50                  55                  60

Arg Pro Gln Ala Pro Asp Leu Tyr Asp Asp Leu Glu Phe Arg Pro
65                  70                  75                  80

Pro Ser Arg Pro Gln Ser Ser Asp Asn Gln Gln Tyr Phe Cys Ala Pro
                85                  90                  95

Ala Pro Leu Ser Pro Ser Ala Arg Pro Arg Ser Pro Trp Gly Lys Leu
            100                 105                 110

Asp Pro Tyr Asp Ser Ser Glu Asp Lys Glu Tyr Val Gly Phe Ala
        115                 120                 125

Thr Leu Pro Asn Gln Val His Arg Lys Ser Val Lys Lys Gly Phe Asp
    130                 135                 140

Phe Thr Leu Met Val Ala Gly Glu Ser Gly Leu Gly Lys Ser Thr Leu
145                 150                 155                 160

Val Asn Ser Leu Phe Leu Thr Asp Leu Tyr Arg Asp Arg Lys Leu Leu
                165                 170                 175
```

-continued

Gly Ala Glu Glu Arg Ile Met Gln Thr Val Glu Ile Thr Lys His Ala
            180                 185                 190

Val Asp Ile Glu Glu Lys Gly Val Arg Leu Arg Leu Thr Ile Val Asp
            195                 200                 205

Thr Pro Gly Phe Gly Asp Ala Val Asn Asn Thr Glu Cys Trp Lys Pro
            210                 215                 220

Val Ala Glu Tyr Ile Asp Gln Gln Phe Glu Gln Tyr Phe Arg Asp Glu
225                 230                 235                 240

Ser Gly Leu Asn Arg Lys Asn Ile Gln Asp Asn Arg Val His Cys Cys
            245                 250                 255

Leu Tyr Phe Ile Ser Pro Phe Gly His Gly Leu Arg Pro Leu Asp Val
            260                 265                 270

Glu Phe Met Lys Ala Leu His Gln Arg Val Asn Ile Val Pro Ile Leu
            275                 280                 285

Ala Lys Ala Asp Thr Leu Thr Pro Pro Glu Val Asp His Lys Lys Arg
            290                 295                 300

Lys Ile Arg Glu Glu Ile Glu His Phe Gly Ile Lys Ile Tyr Gln Phe
305                 310                 315                 320

Pro Asp Cys Asp Ser Asp Glu Asp Glu Asp Phe Lys Leu Gln Asp Gln
            325                 330                 335

Ala Leu Lys Glu Ser Ile Pro Phe Ala Val Ile Gly Ser Asn Thr Val
            340                 345                 350

Val Glu Ala Arg Gly Arg Arg Val Arg Gly Arg Leu Tyr Pro Trp Gly
            355                 360                 365

Ile Val Glu Val Glu Asn Pro Gly His Cys Asp Phe Val Lys Leu Arg
            370                 375                 380

Thr Met Leu Val Arg Thr His Met Gln Asp Leu Lys Asp Val Thr Arg
385                 390                 395                 400

Glu Thr His Tyr Glu Asn Tyr Arg Ala Gln Cys Ile Gln Ser Met Thr
            405                 410                 415

Arg Leu Val Val Lys Glu Arg Asn Arg Asn Lys Leu Thr Arg Glu Ser
            420                 425                 430

Gly Thr Asp Phe Pro Ile Pro Ala Val Pro Pro Gly Thr Asp Pro Glu
            435                 440                 445

Thr Glu Lys Leu Ile Arg Glu Lys Asp Glu Glu Leu Arg Arg Met Gln
            450                 455                 460

Glu Met Leu His Lys Ile Gln Lys Gln Met Lys Glu Asn Tyr
465                 470                 475

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
ctgagcaagt tcgtgaagga tttc                                           24

<210> SEQ ID NO 6
<211> LENGTH: 23
<212> TYPE: DNA
<213> ORGANISM: Artificial Sequence -continued

```
<220> FEATURE:
<223> OTHER INFORMATION: Description of Artificial Sequence: Primer

<400> SEQUENCE: 6
cagtcctctg acaaccagca gta                                              23
```